United States Patent
Smith et al.

(10) Patent No.: US 10,577,427 B2
(45) Date

(56) References Cited

U.S. PATENT DOCUMENTS

| | | |
|---|---|---|
| 9,809,654 B2 | 11/2017 | Robert |
| 9,828,435 B2 | 11/2017 | Evans |
| 9,890,213 B2 | 2/2018 | Smith |
| 9,963,504 B2 | 5/2018 | Klimatcheva |
| 10,111,950 B2 | 10/2018 | Porcelli |
| 10,301,393 B2 | 5/2019 | Smith |
| 2002/0177567 A1 | 11/2002 | Cheever |
| 2003/0044409 A1 | 3/2003 | Carson |
| 2004/0072283 A1 | 4/2004 | Seed |
| 2006/0003316 A1 | 1/2006 | Simard |
| 2006/0263774 A1 | 11/2006 | Clark |
| 2009/0169512 A1 | 7/2009 | Weltzin |
| 2009/0304627 A1 | 12/2009 | Draghia-Akli |
| 2013/0028892 A1 | 1/2013 | MacDonald |
| 2013/0095118 A1 | 4/2013 | Smith |
| 2013/0164325 A1 | 6/2013 | Porcelli |
| 2013/0288927 A1 | 10/2013 | Smith |
| 2013/0302320 A1 | 11/2013 | Smith |
| 2015/0087533 A1 | 3/2015 | Hoogenboom |
| 2019/0169606 A1 | 6/2019 | Smith |

FOREIGN PATENT DOCUMENTS

| | | |
|---|---|---|
| WO | 2005055936 | 6/2005 |
| WO | 2018026715 | 2/2018 |
| WO | 2018156509 | 8/2018 |
| WO | 2018175179 | 9/2018 |
| WO | 2018204895 | 11/2018 |

OTHER PUBLICATIONS

Geada, M., et al., 2001, "Movements of vaccinia virus intracellular enveloped virions with GFP tagged to the F13L envelope protein" Journal of General Virology, 82: 2747-2760.

Husain, M., et al., 2003, "Topology of epitope-tagged F13L protein, a major membrance component of extracellular vaccinia virions" Virology, 308: 233-242.

International Search Report and Written Opinion dated Aug. 16, 2017 issued in PCT Patent Application No. PCT/US2017/028787.

Ward, B., et al., 2001, "Visualization of Intracellular Movement of Vaccinia Virus Virions Containing a Green Fluorescent Protein-B5R Membrane Protein Chimera", Journal of Virology, vol. 75 No. 10: 4802-4813.

Carpentier, D., et al. 2017, "Vaccinia Virus egress mediated by virus protein A36 is reliant on the F12 protein", Journal of General Virology, 98: 1500-1514.

DeHaven, B., et al., 2011, "The vaccinia virus A56 protein: a multifunctional transmembrane glycoprotein that anchors two secreted viral proteins", Journal of General Virology, 92: 1971-1980.

Lorenzo, M., et al., 2000, "Intracellular Localization of Vaccinia Virus Extracellular Enveloped Virus Envelope Proteins Individually Expressed Using a Semliki Forest Virus Replicon", Journal of Virology, vol. 74(22): 10535-10550.

Roberts, et al., 2008, "Vaccinia virus morphogenesis and dissemination", Trends in Microbiology, vol. 16(10): 472-479.

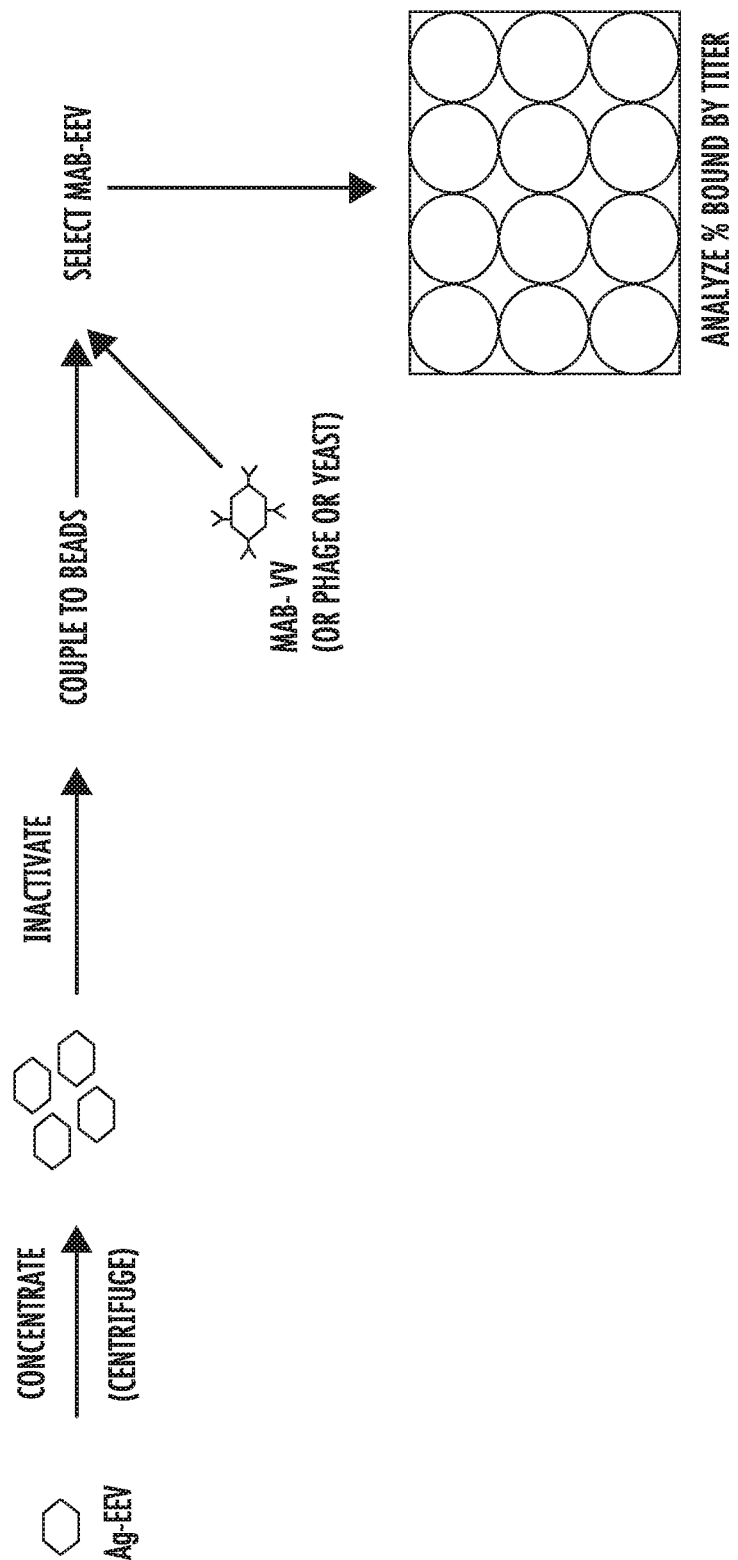

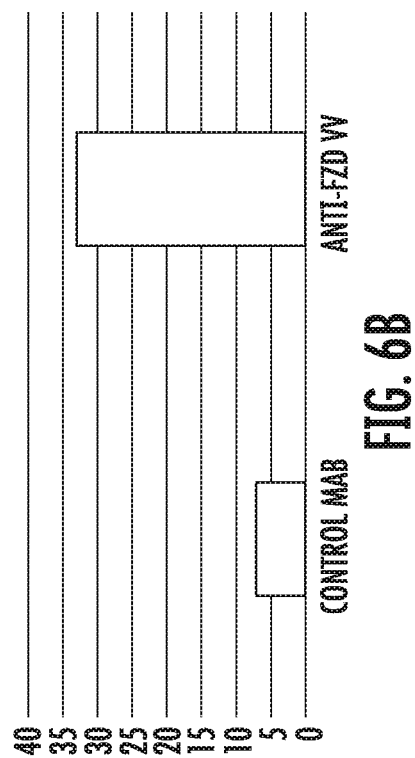
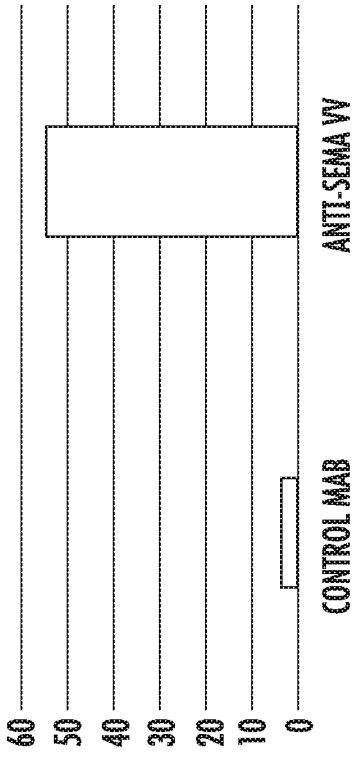
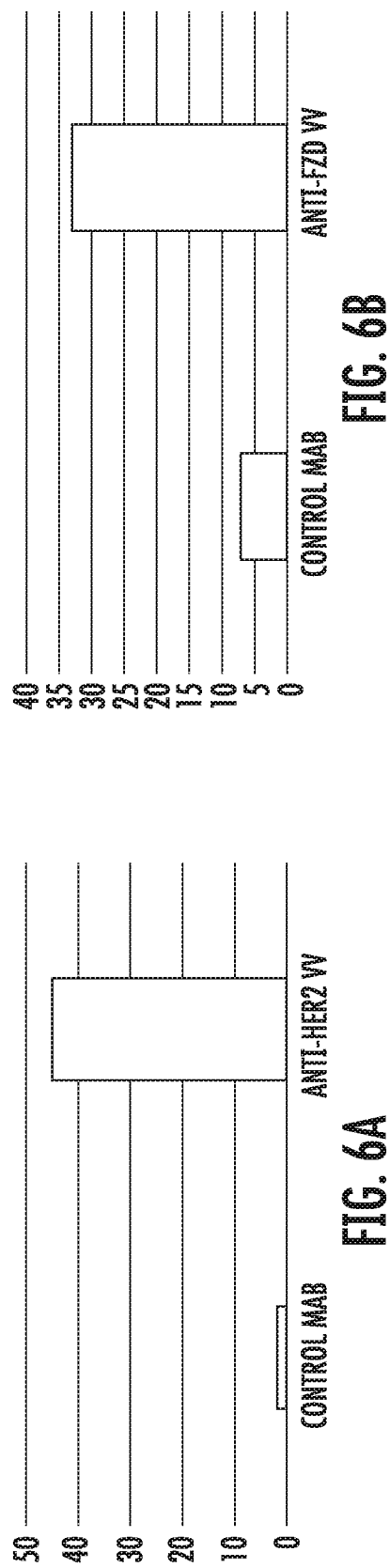
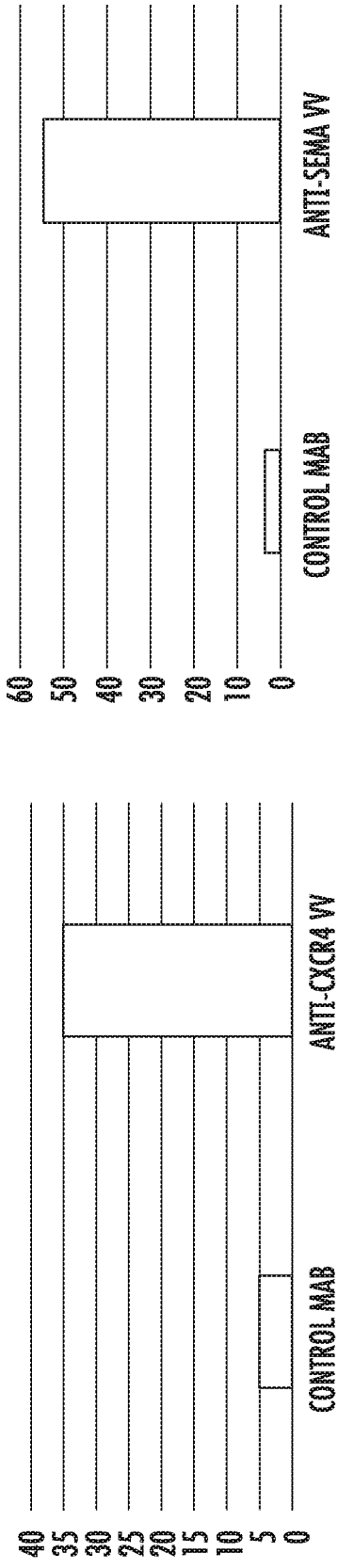

INTEGRAL MEMBRANE PROTEIN DISPLAY ON POXVIRUS EXTRACELLULAR ENVELOPED VIRIONS

CROSS-REFERENCE TO RELATED APPLICATIONS

This application is a US National Stage Entry of PCT Application No. PCT/US2017/028787, filed Apr. 21, 2017, which claims priority benefit of the filing date of U.S. Provisional Patent Application Ser. No. 62/326,501 filed on Apr. 22, 2016, which are each hereby incorporated by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Sep. 8, 2018, is named Sequence-Listing and is 61,440 bytes in size.

BACKGROUND

Antibodies of defined specificity are being employed in an increasing number of diverse therapeutic applications. A number of methods have been used to obtain useful antibodies for human therapeutic use. These include chimeric and humanized antibodies, and fully human antibodies selected from libraries, e.g., phage display libraries, or from transgenic animals. Immunoglobulin libraries constructed in bacteriophage can derive from antibody producing cells of naïve or specifically immunized individuals and could, in principle, include new and diverse pairings of human immunoglobulin heavy and light chains. Although this strategy does not suffer from an intrinsic repertoire limitation, it requires that complementarity determining regions (CDRs) of the expressed immunoglobulin fragment be synthesized and fold properly in bacterial cells. Many antigen binding regions, however, are difficult to assemble correctly as a fusion protein in bacterial cells. In addition, the protein will not undergo normal eukaryotic post-translational modifications. As a result, this method imposes a different selective filter on the antibody specificities that can be obtained. Alternatively, fully human antibodies can be isolated from libraries in eukaryotic systems, e.g., yeast display, retroviral display, or expression in DNA viruses such as poxviruses. See, e.g., U.S. Pat. No. 7,858,559, and U.S. Patent Appl. Publication No. 2013-028892, which are incorporated herein by reference in their entireties.

Many important targets for therapeutic antibodies are integral membrane proteins (IMPs), e.g., multi-pass membrane proteins (GPCRs, Ion Channels, etc.) that are difficult to express and purify in a conformationally-intact state. The absence of properly folded target proteins in an isolated state makes the identification and selection of antibodies to these targets challenging. While certain IMPs can be expressed on the surface of cells, e.g., mammalian cells, whole cells are problematic for use in antibody discovery because they are complex antigen mixtures, target expression can be low, and because certain display packages used to construct antibody libraries (e.g., vaccinia virus antibody libraries) can bind to whole cells non-specifically. There remains a need for new methods to express and display target IMPs of interest in their native conformation at a sufficient concentration and with minimal competition from other cell proteins to allow for identification and selection of therapeutic antibodies and antibody-like molecules from display libraries.

SUMMARY

This disclosure provides compositions and methods for expressing and displaying isolated integral membrane proteins (IMPs) or fragments thereof in a native conformation for use in the screening, selecting, and identifying of antibodies or antibody-like molecules that bind to a target IMP of interest.

In certain embodiments, the disclosure provides an isolated polynucleotide that includes: a first nucleic acid fragment that encodes an integral membrane protein (IMP) or fragment thereof, where the IMP or fragment thereof includes at least one extra-membrane region, at least one transmembrane domain and at least one intra-membrane region, and where a portion of the first nucleic acid fragment encoding at least one intra-membrane region is situated at the 5' or 3' end of the first nucleic acid fragment; and a second nucleic acid fragment that encodes a vaccinia virus F13L protein or functional fragment thereof, where the second nucleic acid fragment is fused in frame to a portion of the first nucleic acid fragment that encodes an intra-membrane region of the IMP. According to these embodiments, a poxvirus infected cell containing the polynucleotide can express an IMP-F13L fusion protein as part of the outer envelope membrane of an extracellular enveloped virion (EEV). In certain aspects, the F13L protein or functional fragment thereof can include the amino acid sequence SEQ ID NO: 1 or a functional fragment thereof. In certain aspects the IMP is a multi-pass membrane protein comprising at least two, at least three, at least four, at least five, at least six or at least seven transmembrane domains. In certain aspects the IMP is a multi-pass membrane protein listed in Table 1.

In certain aspects the multi-pass IMP can have an odd number of transmembrane domains, the 5' end of the first nucleic acid fragment can encode an extra-membrane region, and the 3' end of the first nucleic acid fragment can encode an intra-membrane region fused to the 5' end of the second nucleic acid fragment. In certain aspects the first nucleic acid fragment of this type can encode, e.g., a G-protein coupled receptor (GPCR). In certain aspects the GPCR can be the human frizzled-4 protein (FZD4), or a fragment thereof, and the polynucleotide can encode a polypeptide that includes amino acids 20 to 892 of SEQ ID NO: 2. In certain aspects the polypeptide can further include a signal peptide, e.g., amino acids 1 to 19 of SEQ ID NO: 2. In certain aspects the GPCR can be a CXC chemokine receptor, e.g., CXCR4, or a fragment thereof, and the polynucleotide can encode a polypeptide that includes the amino acid sequence SEQ ID NO: 3.

In certain aspects the multi-pass IMP can have an even number of transmembrane domains, and both the 5' and 3' ends of the first nucleic acid fragment can encode intra-membrane regions. In certain aspects, the second nucleic acid fragment can be fused to 3' end of the first nucleic acid fragment. In certain aspects the IMP can be, e.g., human CD20 protein, or a fragment thereof, and the polynucleotide can encode a polypeptide that includes the amino acid sequence SEQ ID NO: 4.

In certain aspects, the first and second nucleic acid fragments of a polynucleotide provided herein can be directly fused. In certain aspects the polynucleotide as provided herein can include a third nucleic acid fragment encoding a heterologous peptide, e.g., a linker sequence, an amino acid tag or label, or a peptide or polypeptide sequence that facilitates purification, such as a histidine tag. In certain aspects a polynucleotide as provided here can be operably associated with a poxvirus promoter, e.g., a p7.5, a T7, or H5 promoter.

The disclosure further provides an F13L fusion protein encoded by a polynucleotide as provided herein. The disclosure further provides a poxvirus genome, e.g., a vaccinia virus genome, that includes a polynucleotide as provided herein. The disclosure further provides a recombinant vaccinia virus EEV that includes a poxvirus genome as provided herein.

The disclosure further provides a method of producing a recombinant vaccinia virus EEV as provided herein where the method includes infecting a host cell permissive for vaccinia virus infectivity with a vaccinia virus comprising a poxvirus genome as provided herein, and recovering EEV released from the host cell.

The disclosure further provides a method to display an integral membrane protein (IMP) or fragment thereof in a native conformation where the method includes infecting host cells permissive for poxvirus infectivity with a recombinant poxvirus that expresses an IMP or fragment thereof as a fusion protein with poxvirus EEV-specific protein or membrane-associated fragment thereof, where EEV produced by the infected host cell comprise the IMP fusion protein as part of the EEV outer envelope membrane and recovering EEV released from the host cell. In certain aspects the IMP or fragment thereof displays on the surface of the EEV in a native conformation. In certain aspects the EEV-specific protein can be the vaccinia virus A33R protein, A34R protein, A56R protein, B5R protein, A36R protein, F13L protein, any membrane-associated fragment thereof, or any combination thereof.

In certain aspects the EEV-specific protein is F13L (SEQ ID NO: 1) or a functional fragment thereof. In certain aspects the IMP is a multi-pass membrane protein that includes at least two, at least three, at least four, at least five, at least six or at least seven transmembrane domains. In certain aspects the IMP can be a G-protein coupled receptor (GPCR), e.g., human FZD4 or CXCR4 as described above, that includes seven transmembrane domains, and the F13L protein can be fused to the C-terminus of the IMP. In certain aspects the IMP or fragment thereof can have an even number of transmembrane domains, e.g., human CD20 as described above, where both the N-terminus and the C-terminus of the IMP or fragment thereof are intra-membrane, and the F13L can be fused to the N-terminus or the C-terminus of the IMP.

In certain aspects the membrane-associated EEV specific protein fragment can include or consist of the stalk, transmembrane, and intra-membrane domains of the vaccinia virus A56R protein, e.g., amino acids 108 to 314 of SEQ ID NO: 5. In certain aspects IMP portion of the A56R fusion protein can include the extracellular domain of human FZD4, e.g., the fusion protein can include amino acids 20 to 370 of SEQ ID NO: 6, the extracellular domain of human ErbB2 (Her2), e.g., the fusion protein can include amino acids 20 to 855 of SEQ ID NO: 7, or the extracellular domain of human CD100 (Semaphorin 4D), e.g., the fusion protein can include amino acids 20 to 935 of SEQ ID NO: 8.

In certain aspects the membrane-associated EEV specific protein fragment can include or consist of the transmembrane and intra-membrane domains, or the stalk, transmembrane, and intra-membrane domains of the vaccinia virus B5R protein, e.g., amino acids 276 to 317 of SEQ ID NO: 9 or amino acids 238 to 317 of SEQ ID NO: 9, respectively. In certain aspects the IMP portion of the B5R fusion protein can include the extracellular domain of human FZD4, e.g., the fusion protein can includes amino acids 20 to 243 of SEQ ID NO: 10 or amino acids 20 to 281 of SEQ ID NO: 11.

The disclosure further provides a fusion protein comprising: amino acids 20 to 892 of SEQ ID NO: 2; SEQ ID NO: 3; SEQ ID NO: 4; amino acids 20 to 370 of SEQ ID NO: 6; amino acids 20 to 855 of SEQ ID NO: 7; amino acids 20 to 935 of SEQ ID NO: 8; amino acids 20 to 243 of SEQ ID NO: 10; amino acids 20 to 281 of SEQ ID NO: 11, amino acids 20 to 506 of SEQ ID NO: 16, or amino acids 20 to 235 of SEQ ID NO: 17. A fusion protein as provided, when expressed by a recombinant poxvirus, e.g., a vaccinia virus, can appear on the surface of a poxvirus extracellular enveloped virion (EEV) in a native conformation. A recombinant poxvirus EEV comprising the fusion protein is also provided. The disclosure further provides a recombinant poxvirus EEV that includes a heterologous IMP or fragment thereof fused to a poxvirus EEV-specific protein or membrane-associated fragment thereof, where the fusion protein is situated in the EEV outer envelope membrane, and where the IMP or fragment thereof displays on the surface of the EEV in its native conformation. In certain aspects the recombinant poxvirus EEV is a vaccinia virus EEV.

The disclosure further provides a method to select antibodies that bind to a multi-pass membrane protein where the method includes attaching recombinant EEV as provided herein to a solid support; providing an antibody display library, where the library comprises display packages displaying a plurality of antigen binding domains; contacting the display library with the EEV such that display packages displaying antigen binding domains that specifically binds to the IMP expressed on the EEV can bind thereto; removing unbound display packages; and recovering display packages that display an antigen binding domain specific for the IMP expressed on the EEV. In certain aspects of this method the recombinant EEV are inactivated prior to attachment to the solid support, e.g., by incubation with Psoralen (Trioxsalen, 4'-aminomethyl-, hydrochloride) in the presence of UV irradiation. In certain aspects of this method the recombinant EEV are attached to the solid surface via reaction with tosyl groups attached to the surface. In certain aspects the solid surface can be tosyl-activated magnetic beads. In certain aspects of this method the recombinant EEV are biotinylated and attached to a streptavidin coated solid surface, e.g., streptavidin-coated magnetic beads.

BRIEF DESCRIPTION OF THE DRAWINGS/FIGURES

FIG. 1A-C: Diagrammatic depiction of integral membrane proteins (IMPs) or fragment thereof fused to vaccinia virus extracellular enveloped virion (EEV)-specific proteins or fragments thereof. The parallel horizontal lines are a diagram of the EEV outer membrane. FIG. 1A diagrams the extracellular domain (ECD) of an IMP fused to a fragment of the vaccinia A56R protein that includes the transmembrane domain and the intra-membrane domain. FIG. 1B diagrams the topology of a typical G protein-coupled receptor fused to the vaccinia virus EEV-specific F13L protein. F13L is associated with the inner side of the EEV outer membrane via palmitoylation. FIG. 1C diagrams the topology of an IMP with an even number of transmembrane domains, e.g., CD20), fused to F13L.

FIG. 2: Demonstration of incorporation of CD20-F13L and CD20 ECD-A56R fusion proteins into vaccinia virus EEV particles.

FIG. 3A: Demonstration of preferential incorporation of CD20-F13L fusion protein over untagged CD20 into vaccinia virus EEV particles.

FIG. 3B: Demonstration of preferential incorporation of FZD4-F13L fusion protein over untagged (unfused) FZD4 into vaccinia virus EEV particles.

FIG. 4: Incorporation of additional IMP-EEV protein fusions into vaccinia virus EEV. "CD20" is a CD20-F13L fusion protein, "CXCR4" is a CXCR4-F13L fusion protein, "Her2" is a Her2 ECD-A56R fusion protein; and "CD100" is a CD100 ECD-A56R fusion protein.

FIG. 5: Outline of assay for screening an antibody display library for display packages that bind to an IMP of interest expressed on vaccinia virus EEV.

FIG. 6A: Binding of vaccinia virus EEV expressing an anti-HER-2 antibody to vaccinia virus EEV expressing the HER2 ECD as a fusion with the vaccinia virus A56R protein, bound by tosyl-groups to magnetic beads.

FIG. 6B: Binding of vaccinia virus EEV expressing an anti-FZD antibody to vaccinia virus EEV expressing FZD4 as a fusion with the vaccinia virus F13L protein, bound by tosyl-groups to magnetic beads.

FIG. 6C: Binding of vaccinia virus EEV expressing an anti-CXCR4 antibody to vaccinia virus EEV expressing the CXCR4 as a fusion with the vaccinia virus F13L protein, bound by tosyl-groups to magnetic beads.

FIG. 6D: Binding of vaccinia virus EEV expressing an anti-CD100 ("sema") antibody to vaccinia virus EEV expressing the CD100 ECD as a fusion with the vaccinia virus A56R protein, bound by tosyl-groups to magnetic beads.

FIG. 7: FACS scans showing enrichment for anti FZD4 antibodies following panning on inactivated FZD-ECD-A45R-expressing EEV bound by tosyl-groups to magnetic beads after 3 (Rd3), 4 (Rd4), and 5 (Rd5) rounds of panning. The top row shows antibody-expressing virus-infected cells stained with 10 µg/ml FZD-His, followed by anti-His-Dyelight650 and anti-Fab-FITC. The bottom row shows antibody-expressing virus-infected cells stained with 10 µg/ml CD100-His (negative control), followed by anti-His-Dyelight650 and anti-Fab-FITC.

FIG. 8: Incorporation two different protein fusions (HA-A56R fusion and FZD4-F13L fusion) into vaccinia virus EEV. EEV expressing the HA-A56R fusion alone, the FZD4-F13L fusion alone, or both fusion proteins, were tested for binding to either anti-FZD4-coated beads or anti-HA coated beads.

FIG. 9: Specific recovery of anti-CXCR4-expressing EEV by magnetic beads coated with EEV expressing both an HA-A56R fusion and CXCR4-F13L fusion. The antigen-EEV were coupled to anti-HA coated beads.

FIG. 10: Binding of biotinylated vaccinia virus EEV expressing the designated fusion proteins to streptavidin coated magnetic beads.

DETAILED DESCRIPTION

Figure 1C:
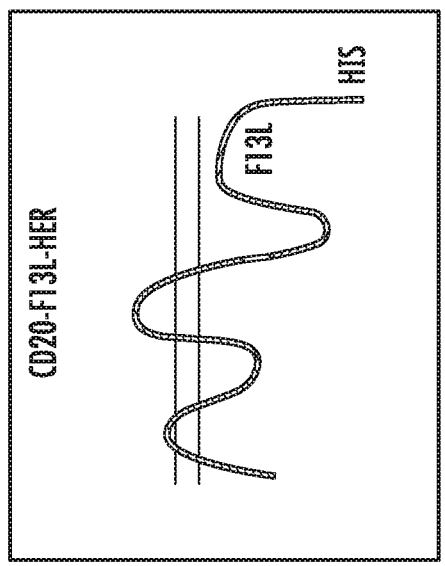

This disclosure provides methods and compositions for expressing and displaying integral membrane proteins (IMPs), e.g., multi-pass (IMPs), in a conformationally intact or native state on the surface of extracellular enveloped virion particles (EEV) of poxviruses, e.g., vaccinia virus, as a fusion with a polypeptide segment an EEV-specific membrane-associated protein, e.g., F13L.

Definitions

The term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides that retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions that do not eliminate antigen binding are well-known in the art (see, e.g., Brummell et al., *Biochem.* 32:1180-1 187 (1993); Kobayashi et al., *Protein Eng.* 12(10):879-884 (1999); and Burks et al., *Proc. Natl. Acad. Sci. USA* 94:412-417 (1997)).

As used herein the term "integral membrane protein" or "IMP" refers to a protein or polypeptide that is attached to a biological membrane. One example of an IMP is a transmembrane protein, which spans the lipid bilayer of the biological membrane one or more times. Single-pass membrane proteins cross the membrane only once, while multi-pass membrane proteins weave in and out, crossing several times. Type I single-pass proteins are positioned with their amino terminus on the outer side of the membrane or "extra-membrane" and their carboxyl-terminus on the interior side of the membrane, or "intra-membrane." Type II single-pass proteins have their amino-terminus on the intra-membrane side. Multi-pass transmembrane proteins pass through the membrane two or more times and can have a variety of different topologies. Those proteins with an even number of transmembrane domains will have both their amino terminus and carboxy terminus on the same side of the membrane. One example of such a protein is CD20, which is expressed on B cells. Those with an odd number of transmembrane domains will have their amino- and carboxy termini on opposite sides of the membrane. Examples include G-protein coupled receptors, which typically have 7 transmembrane domains, with the amino terminus on the extra-membrane side and the carboxy terminus on the intra-membrane side. Certain IMPs do not have transmembrane domains and are instead anchored to the membrane, e.g., via a lipid such as glycosylphosphatidylinositol or palmitoyl group. IMPs have myriad biological functions including, but not limited to transporters, linkers, channels, receptors, enzymes, energy transduction or cell adhesion.

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, that has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Poxvirus promoters (e.g. p7.5 or H5) or the bacteriophage T7 promoter can also be used as transcription control regions. When employing a T7 promoter, an inducible vaccinia expression system can be utilized. The vaccinia expression system can include, but is not limited, to a first recombinant vaccinia virus that encodes the entire bacteriophage T7 gene 1 coding region for T7 RNA polymerase, and a second recombinant vaccinia virus that encodes a gene of interest flanked by a T7 promoter and termination regulatory elements. Dual infection of eukaryotic cells with both recombinant vaccinia viruses results in synthesis of the T7 RNA polymerase and expression of the gene of interest controlled by the T7 promoter.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions that encode secretory or signal peptides, which direct the secretion of a polypeptide encoded by a polynucleotide as disclosed herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

As used herein, a "library" is a representative genus of polynucleotides, e.g., a group of polynucleotides related through, for example, their origin from a single animal species, tissue type, organ, or cell type, where the library collectively comprises at least two different species within a given genus of polynucleotides. A library of polynucleotides can include, e.g., at least two, at least 5, at least 10, 100, $10^3$, $10^4$, $10^5$, $10^6$, $10^7$, $10^8$, or $10^9$ different species within a given genus of polynucleotides. In certain aspects, a library of polynucleotides as provided herein can encode a plurality of polypeptides that contains a polypeptide of interest. In certain aspects, a library of polynucleotides as provided herein can encode a plurality of immunoglobulin subunit polypeptides, e.g., heavy chain subunit polypeptides or light chain subunit polypeptides. In this context, a "library" as provided herein comprises polynucleotides of a common genus, the genus being polynucleotides encoding immunoglobulin subunit polypeptides of a certain type and class e.g., a library might encode a human μ, γ-1, γ-2, γ-3, γ-4, α-1, α-2, ε, or δ heavy chain, or a human κ or λ light chain. Although each member of any one library constructed according to the methods provided herein can encode the same heavy or light chain constant region and/or a membrane anchoring domain, the library can collectively comprise at least two, at least 5, or at least 10, 100, $10^3$, $10^4$, $10^5$, $10^6$, $10^7$, $10^8$, or $10^9$ different variable region associated with the common constant region.

In other embodiments, the library can a plurality of immunoglobulin single-chain fragments that comprise a variable region, such as a light chain variable region or a heavy chain variable region, and/or both a light chain variable region and a heavy chain variable region, e.g., an ScFv fragment.

As used herein, a "display library" is a library of polynucleotides each carried in a "display package" that expresses the polypeptide encoded by the library polynucleotide on its surface. An antibody display library, for example, can include plurality of display packages, each displaying an antigen binding domain of an antibody on its surface. When the display library is permitted to interact with an antigen of interest, e.g., immobilized on a solid surface, those display packages that bind the antigen can be isolated from the rest of the library and recovered. The polynucleotide encoding the antigen binding domain displayed on the surface of the display package can then be isolated. Display libraries include, without limitation, phage display libraries in bacteria or libraries in eukaryotic systems, e.g., yeast display, retroviral display, or expression in DNA viruses such as poxviruses. See, e.g., U.S. Pat. No. 7,858,559, and U.S. Patent Appl. Publication No. 2013-028892, which are incorporated herein by reference in their entireties. In certain aspects, an antibody display library can be prepared in a poxvirus, e.g., vaccinia virus vector, as fusion proteins with an EEV-specific protein, such that the "display packages" are EEV particles. See U.S. Patent Appl. Publication No. 2013-028892.

Such display libraries can be screened against the IMP fusion proteins displayed on the surface of EEV as provided herein.

By "recipient cell" or "host cell" or "cell" is meant a cell or population of cells in which a recombinant protein can be expressed, a virus can be propagated, or polynucleotide libraries as provided herein can be constructed and/or propagated. A host cell as provided herein is typically a eukaryotic cell or cell line, e.g., a vertebrate, mammalian, rodent, mouse, primate, or human cell or cell line. By "a population of host cells" is meant a group of cultured cells which a "library" as provided herein can be constructed, propagated, and/or expressed. Any host cell which is permissive for vaccinia virus infectivity is suitable for the methods provided by this disclosure. Host cells for use in the methods provided herein can be adherent, e.g., host cells that grow attached to a solid substrate, or, alternatively, the host cells can be in suspension.

Host cells as provided herein can comprise a constitutive secretory pathway, where proteins, e.g., proteins of interest expressed by the cell or by a library, are secreted from the interior of the cell either to be expressed on a cell or viral membrane surface or to be fully secreted as soluble polypeptides. In certain aspects, proteins of interest expressed on or in a biological membrane, e.g., an IMP, are expressed on the surface of an enveloped virus produced by the host cell, e.g., an extracellular enveloped vaccinia virus, or EEV. IMPS can follow the same pathway as fully secreted forms or proteins, passing through to the ER lumen, except that they can be retained in the ER membrane by the presence of one or more stop-transfer signals, or "transmembrane domains." Transmembrane domains are hydrophobic stretches of about 20 amino acids that adopt an alpha-helical conformation as they transverse the membrane. Membrane embedded proteins are anchored in the phospholipid bilayer of the plasma membrane. Transmembrane forms of polypeptides of interest, e.g., membrane-anchored immunoglobulin heavy chain polypeptides typically utilize amino terminal signal peptides as do fully secreted forms.

Signal peptides, transmembrane domains, and cytosolic or "intra-membrane" domains are known for a wide variety of membrane bound and/or fully secreted proteins.

Suitable transmembrane domains can include, but are not limited to the TM domain of the vaccinia virus EEV-specific HA protein A56R, or the EEV-specific vaccinia virus transmembrane proteins A33R, A34R, A36R, or B5R. See, e.g., U.S. Patent Appl. Publ. No. 2013/0288927, published Oct. 31, 2013, and incorporated herein by reference in its entirety. In certain aspects the EEV specific protein can be anchored to the inner surface of the viral envelope via a palmitoyl group, e.g., the vaccinia virus protein F13L, discussed in more detail elsewhere herein.

As used herein, the term "binding molecule" refers in its broadest sense to a molecule that specifically binds to a receptor, e.g., an epitope or an antigenic determinant. As described further herein, a binding molecule can comprise one or more "antigen binding domains" described herein. A non-limiting example of a binding molecule is an antibody or fragment thereof that retains antigen-specific binding.

The terms "binding domain" and "antigen binding domain" are used interchangeably herein and refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain."

Other antigen binding domains include, without limitation, the variable heavy chain (VHH) of an antibody derived from a camelid species, or six immunoglobulin complementarity determining regions (CDRs) expressed in a fibronectin scaffold.

The terms "antibody" and "immunoglobulin" can be used interchangeably herein. An antibody (or a fragment, variant, or derivative thereof as disclosed herein) includes at least the variable region of a heavy chain (e.g., for camelid species)

or at least the variable regions of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen binding fragment of an antibody to a full sized antibody, e.g., an IgG antibody that includes two complete heavy chains and two complete light chains.

The term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2)). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, $IgA_2$, etc. are well characterized and are known to confer functional specialization.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three dimensional structural characteristics, and or specific charge characteristics. An epitope is a region of a target that is bound by an antibody.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Both the light and heavy chains are divided into regions of structural and functional homology. The terms "constant" and "variable" are used functionally. In this regard, it will be appreciated that the variable regions (which can be called "variable domains" interchangeably herein) of both the variable light (VL) and variable heavy (VH) chain portions determine antigen recognition and specificity. Conversely, the constant domains of the light chain (CL) and the heavy chain (e.g., CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains are at the carboxy-terminus of the heavy and light chain, respectively.

The six "complementarity determining regions" or "CDRs" present in an antibody antigen binding domain are short, non-contiguous sequences of amino acids that are specifically positioned to form the antigen binding domain as the antibody assumes its three dimensional configuration in an aqueous environment. The remainder of the amino acids in the antigen binding domain, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., J. Mol. Biol. 196:901-917 (1987), which are incorporated herein by reference. Immunoglobulin variable domains can also be analyzed, e.g., using the IMGT information system (wwww://imgt.cines.fr/) (IMGT®/V-Quest) to identify variable region segments, including CDRs. (See, e.g., Brochet et al., Nucl. Acids Res., 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen binding fragments, variants, or derivatives thereof include, but are not limited to, polyclonal, monoclonal, human, humanized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), single domain antibodies such as camelid VHH antibodies, fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule. Also contemplated are immunoglobulin new antigen receptor (IgNAR) isotypes that are bivalent and comprise a single chain that includes an IgNAR variable domain (VNAR). (See, Walsh et al., *Virology* 411: 132-141, 2011).

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

As used herein, the term "affinity" refers to a measure of the strength of the binding of an individual epitope with one or more antigen binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

As used herein, the term "heavy chain subunit" or "heavy chain domain" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof.

As used herein, the term "light chain subunit" or "light chain domain" includes amino acid sequences derived from an immunoglobulin light chain. The light chain subunit includes at least one of a VL or CL (e.g., Cκ or Cλ) domain.

Binding molecules, e.g., antibodies or antigen binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments can be physically or spatially separated by, for example, in-frame linker sequence. For example, polynucleotides encoding an IMP and a vaccinia virus EEV-specific protein can be fused, in-frame, but be separated by a polynucleotide encoding a linker or spacer, as long as the "fused" open reading frames are co-translated as part of a continuous polypeptide.

As used herein, the term "hemagglutinin tag" or "HA tag" is a protein derived from a human influenza hemagglutinin surface glycoprotein (HA) corresponding to amino acids 98-106. The HA tag is extensively used as a general epitope tag in expression vectors. Recombinant proteins can be engineered to express the HA tag, which does not appear to interfere with the bioactivity or the biodistribution of the recombinant protein. This tag facilitates the detection, isolation, and purification of the protein of interest.

In the context of polypeptides, a "linear sequence" or a "sequence" is an order of amino acids in a polypeptide from the amino or N-terminus to the carboxyl or C-terminus, in which amino acids that neighbor each other in the sequence are contiguous in the primary structure of the polypeptide.

A portion of a polypeptide that is "amino-terminal" or "N-terminal" to another portion of a polypeptide is that portion that comes earlier in the sequential polypeptide chain. Similarly a portion of a polypeptide that is "carboxy-terminal" or "C-terminal" to another portion of a polypeptide is that portion that comes later in the sequential polypeptide chain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "eukaryote" or "eukaryotic organism" is intended to encompass all organisms in the animal, plant, and protist kingdoms, including protozoa, fungi, yeasts, green algae, single celled plants, multi celled plants, and all animals, both vertebrates and invertebrates. The term does not encompass bacteria or viruses. A "eukaryotic cell" is intended to encompass a singular "eukaryotic cell" as well as plural "eukaryotic cells," and comprises cells derived from a eukaryote.

The term "vertebrate" is intended to encompass a singular "vertebrate" as well as plural "vertebrates," and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In certain aspects, the mammal is a human subject.

The terms "tissue culture" or "cell culture" or "culture" or "culturing" refer to the maintenance or growth of plant or animal tissue or cells in vitro under conditions that allow preservation of cell architecture, preservation of cell function, further differentiation, or all three. "Primary tissue cells" are those taken directly from tissue, i.e., a population of cells of the same kind performing the same function in an organism. Treating such tissue cells with the proteolytic enzyme trypsin, for example, dissociates them into individual primary tissue cells that grow or maintain cell architecture when seeded onto culture plates. Cell cultures arising from multiplication of primary cells in tissue culture are called "secondary cell cultures." Most secondary cells divide a finite number of times and then die. A few secondary cells, however, can pass through this "crisis period," after which they are able to multiply indefinitely to form a continuous "cell line." The liquid medium in which cells are cultured is referred to herein as "culture medium" or "culture media." Culture medium into which desired molecules, e.g., viruses or proteins, e.g., immunoglobulin molecules, have been secreted during culture of the cells therein can be referred to as "conditioned medium."

As used herein, the term "identify" refers to methods in which a desired molecule, e.g., a polynucleotide encoding a protein of interest with a desired characteristics or function, is differentiated from a plurality or library of such molecules. Identification methods include "selection" and "screening" or "panning." As used herein, "selection" methods are those in which the desired molecules can be directly separated from the library, e.g., via drug resistance. As used herein, "screening" or "panning" methods are those in which pools comprising the desired molecules are subjected to an assay in which the desired molecule can be detected. Aliquots of the pools in which the molecule is detected are then divided into successively smaller pools which are likewise assayed, until a pool which is highly enriched from the desired molecule is achieved.

Poxviruses, e.g., Vaccinia Virus EEV Vectors

IMP fusion proteins as provided herein are produced in poxvirus vectors, e.g., vaccinia virus vectors. The term "poxvirus" includes any member of the family Poxviridae. See, for example, B. Moss in: Virology, 2d Edition, B. N. Fields, D. M. Knipe et al., Eds., Raven Press, p. 2080 (1990). The genus of orthopoxvirus includes, e.g., vaccinia virus, variola virus (the virus that causes smallpox), and raccoon poxvirus. Vaccinia virus is the prototype orthopoxvirus, and has been developed and is well-characterized as a vector for the expression of heterologous proteins.

In those embodiments where poxvirus vectors, in particular vaccinia virus vectors, are used to express IMP fusion proteins as provided herein, any suitable poxvirus vector can be used. In certain aspects, the location of a gene encoding an IMP fusion protein can be in a region of the vector that is non-essential for growth and replication of the virus so that infectious viruses are produced. Although a variety of non-essential regions of the vaccinia virus genome have been characterized, the most widely used locus for insertion of foreign genes is the thymidine kinase locus, located in the HindIII J fragment in the genome. In certain vaccinia virus vectors, the tk locus has been engineered to contain one or two unique restriction enzyme sites, allowing for convenient use of the trimolecular recombination method recombinant virus production, as described elsewhere herein.

Polynucleotides encoding IMP fusion proteins as provided herein can be inserted into poxvirus vectors, particularly vaccinia virus vectors, under operable association with a transcriptional control region which functions in the cytoplasm of a poxvirus-infected cell.

Poxvirus transcriptional control regions comprise a promoter and a transcription termination signal. Gene expression in poxviruses is temporally regulated, and promoters for early, intermediate, and late genes possess varying structures. Certain poxvirus genes are expressed constitutively, and promoters for these "early-late" genes bear hybrid structures. Synthetic early-late promoters have also been developed. Suitable poxvirus promoters for expressing IMP fusion proteins as provided herein include, but are not limited to late promoters such as the 7.5-kD promoter, the MIL promoter, the 37-kD promoter, the 11-kD promoter, the 11L promoter, the 12L promoter, the 13L promoter, the 15L promoter, the 17L promoter, the 28-kD promoter, the H1L promoter, the H3L promoter, the H5L promoter, the H6L promoter, the H8L promoter, the D11L promoter, the D12L promoter, the D13L promoter, the A1L promoter, the A2L promoter, the A3L promoter, and the P4b promoter. See, e.g., Moss, B., "Poxviridae and their Replication" IN Virology, 2d Edition, B. N. Fields, D. M. Knipe et al., Eds., Raven Press, p. 2090 (1990).

Suitable poxvirus vectors include wild-type vaccinia virus, e.g., strain Western Reserve or WR, or attenuated vaccinia virus, e.g., modified vaccinia Ankara (MVA) (Mayr, A. et al., Infection 3:6-14 (1975)).

During its replication cycle, a poxvirus, e.g., a vaccinia virus, produces four infectious forms which differ in their membrane structure: intracellular mature virion (IMV), the intracellular enveloped virion (IEV), the cell-associated enveloped virion (CEV) and the extracellular enveloped virion (EEV). The prevailing view is that the IMV have a single lipoprotein membrane, while the CEV and EEV are both surrounded by two membrane layers and the IEV has three envelopes. EEV is shed from the plasma membrane of the host cell and the EEV membrane is derived from the trans-Golgi.

After infection, the virus loses its membrane(s) and the DNA/protein core is transported along microtubules into the cell. The proteins encoded by early vaccinia mRNAs ("early" is defined as pre-DNA replication) lead to uncoating of the vaccinia core and subsequent DNA replication. This replication occurs in what are termed "viral factories" which are located essentially on top of the ER. Within the viral factory, immature virions (IV) assemble and are processed to form IMV (Intracellular Mature Virus). IMVs contain a membrane that is derived from the ER. The majority of IMVs are released from the cell by cell lysis. Some IMVs are transported on microtubules to sites of wrapping by membranes of the trans-Golgi network or early endosomes. The wrapping of the IMV particles by a double membrane creates a form of vaccinia called IEVs (Intracellular Enveloped Virus). The IEVs are then transported to the cell surface on microtubules. The outer IEV membrane fuses with the plasma membrane to expose a CEV (Cell Associated Enveloped Virus) at the cell surface. Actin polymerization from the host cell can drive the CEV to infect neighboring cells, or the virus can be released as an EEV. See, e.g., Kim L. Roberts and Geoffrey L. Smith. Trends in Microbiology 16(10):472-479 (2008); Geoffrey L. Smith, et al., Journal of General Virology 83:2915-2931 (2002).

At least six virus-encoded proteins have been reported as components of the EEV envelope membrane. Of these, four proteins (A33R, A34R, A56R, and B5R) are glycoproteins, one (A36R) is a nonglycosylated transmembrane protein, and one (F13L) is a palmitoylated peripheral membrane protein. See, e.g., Lorenzo et al., Journal of Virology 74(22): 10535 (2000). During infection, these proteins localize to the Golgi complex, where they are incorporated into infectious virus that is then transported and released into the extracellular medium. As provided herein, IMP fusion proteins are directed to and expressed on the EEV membrane as a fusion protein with an EEV-specific protein, e.g., F13L or A56R.

The F13L protein is associated with the interior surface of the outermost EEV membrane through palmitoylation of cysteines 185 and 186. Smith *Trends in Microbiol.* 16:472-479 (2008). Vaccinia viruses in which the gene encoding F13L is deleted form tiny plaques and the number of EEV produced is reduced significantly.

The amino acid sequence of the F13L protein from vaccinia virus strain WR is presented as SEQ ID NO: 1. The two palmitoylated cysteine residues (amino acids 85 and 86 of SEQ ID NO: 1) are underlined. Since F13L does not cross the membrane, it does not have a transmembrane domain or signal peptide.

>F13L
(SEQ ID NO: 1)
MWPFASVPAGAKCRLVETLPENMDFRSDHLTTFECFNEIITL

AKKYIYIASFCCNPLSTTRGALIFDKLKEASEKGIKIIVLLDER

GKRNLGELQSHCPDINFITVNIDKKNNVGLLLGCFWVSDDE

RCYVGNASFTGGSIHTIKTLGVYSDYPPLATDLRRRFDTFKA

FNSAKNSWLNLCSAA<u>CC</u>LPVSTAYHIKNPIGGVFFTDSPEHL

LGYSRDLDTDVVIDKLKSAKTSIDIEHLAIVPTTRVDGNSYY

WPDIYNSIIEAAINRGVKIRLLVGNWDKNDVYSMATARSLD

ALCVQNDLSVKVFTIQNNTKLLIVDDEYVHITSANFDGTHY

QNHGFVSFNSIDKQLVSEAKKIFERDWVSSHSKSLKI

The A56R protein is the vaccinia virus hemagglutinin, and is a standard type I integral membrane protein comprising an amino-terminal extracellular ("extra-membrane") domain, a single transmembrane domain, and a cytoplasmic ("intra-membrane") domain. A56R comprises an N-terminal signal peptide of about 33 amino acids, an Ig-like domain extending from about amino acid 34 to about amino acid 103, a stalk region extending from about amino acid 121 to about amino acid 275, a transmembrane domain extending from about amino acid 276 to about amino acid 303, and an cytoplasmic ("inter-membrane") domain extending from about amino acid 304 to amino acid 314. See DeHaven et al., *J. Gen Virol.* 92:1971-1980 (2011). A56R is presented as SEQ ID NO: 5.

>A56R
(SEQ ID NO: 5)
MTRLPILLLLISLVYATPFPQTSKKIGDDATLSCNRNNTNDY

VVMSAWYKEPNSIILLAAKSDVLYFDNYTKDKISYDSPYDD

LVTTITIKSLTARDAGTYVCAFFMTSTTNDTDKVDYEEYSTE

LIVNTDSESTIDIILSGSTHSPETSSKKPDYIDNSNCSSVFEIAT

PEPITDNVEDHTDTVTYTSDSINTVSASSGESTTDETPEPITD

KEDHTVTDTVSYTTVSTSSGIVTTKSTTDDADLYDTYNDND

TVPPTTVGGSTTSISNYKTKDFVEIFGITALIILSAVAIFCITYY

IYNKRSRKYKTENKV

IMP fusion proteins as provided herein can be expressed in any suitable vaccinia virus. In certain embodiments, the DNA encoding an EEV fusion protein can be inserted into a region of the vaccinia virus genome which is non-essential for growth and replication of the vector so that infectious viruses are produced. Although a variety of non-essential regions of the vaccinia virus genome have been characterized, the most widely used locus for insertion of foreign genes is the thymidine kinase locus, located in the HindIII J fragment in the genome. IMP fusion proteins as provided herein can be inserted into vaccinia virus vectors under operable association with a transcriptional control region which functions in the cytoplasm of a poxvirus-infected cell.

Suitable promoters for use in the methods described herein include, without limitation, the early/late 7.5-kD promoter, or the early/late H5 promoter (or variants thereof).

The Tri-Molecular Recombination Method

Tri-molecular recombination, as disclosed in Zauderer, PCT Publication No. WO 00/028016 and in U.S. Pat. No. 7,858,559, is a high efficiency, high titer-producing method for expressing proteins of interest and or producing libraries in vaccinia virus. The tri-molecular recombination method allows the generation of recombinant viruses at efficiencies of at least 90%, and titers at least at least 2 orders of magnitude higher than those obtained by direct ligation.

In certain aspects, IMP fusion proteins for expression in vaccinia virus and display on EEV as described herein can be constructed in poxvirus vectors, e.g., vaccinia virus vectors, by tri-molecular recombination.

In certain embodiments, a transfer plasmid for IMP fusion proteins for expression in EEV is provided, which comprises a polynucleotide flanking regions in the vaccinia virus Tk gene, the vaccinia virus H5 promoter, and NcoI and BsiWI restriction sites for inserting coding regions for desired fusion proteins.

Integral Membrane Proteins

The disclosure provides a method for expressing integral membrane proteins (IMPS) in a conformationally intact state that approaches the native conformation of the protein as it would appear in a cell in which the protein is naturally expressed. According to the disclosure, IMPs are expressed as fusion proteins with poxvirus proteins that are expressed on poxvirus, e.g., vaccinia virus EEVs. IMP fusion proteins as provided herein, when expressed and displayed on the surface of EEVs, are useful as target antigens for screening libraries of binding molecules, e.g., antibody display libraries.

Any IMP can be constructed as a fusion protein according to the methods provided herein. In certain aspects the IMP is a target for immunotherapy. In certain aspects the IMP is a multi-pass IMP such as CD20 or a G-protein coupled receptor (GPCR). Suitable multi-pass human IMPS for use in the construction of IMP fusion proteins as provided herein include, without limitation, the proteins listed in Table 1.

TABLE 1

Exemplary Human Multi-Pass Integral Membrane Proteins

| Protein Name | ENTREZ_gene_ID | ENTREZ gene symbol | # predicted TM domains |
|---|---|---|---|
| Poliovirus receptor-related protein 3 | 25945 | PVRL3 | 2 |
| Prominin-1 | 8842 | PROM1 | 5 |
| FL cytokine receptor | 2322 | FLT3 | 2 |
| Scavenger receptor cysteine-rich type 1 protein M130 | 9332 | CD163 | 2 |
| C-X-C chemokine receptor type 1 | 3577 | CXCR1 | 6 |
| C-X-C chemokine receptor type 3 | 2833 | CXCR3 | 7 |
| C-X-C chemokine receptor type 5 | 643 | CXCR5 | 7 |
| C-C chemokine receptor type 4 | 1233 | CCR4 | 7 |
| C-C chemokine receptor type 7 | 1236 | CCR7 | 7 |
| B-lymphocyte antigen CD20 | 931 | MS4A1 | 4 |
| Major prion protein | 5621 | PRNP | 2 |
| Plexin-C1 | 10154 | PLXNC1 | 2 |
| Multidrug resistance protein 1 | 5243 | ABCB1 | 12 |
| Putative G-protein coupled receptor 44 | 11251 | GPR44 | 7 |
| EGF-like module-containing mucin-like hormone receptor-like 2 | 30817 | EMR2 | 7 |
| Frizzled-4 | 8322 | FZD4 | 9 |
| Leukocyte surface antigen CD47 | 961 | CD47 | 5 |
| CD63 antigen | 967 | CD63 | 4 |
| Choline transporter-like protein 1 | 23446 | SLC44A1 | 9 |
| CD97 antigen | 976 | CD97 | 7 |
| Multidrug resistance-associated protein 1 | 4363 | ABCC1 | 16 |
| CAS1 domain-containing protein 1 | 64982 | CASD1 | 14 |
| Solute carrier family 12 member 6 | 9990 | SLC12A6 | 14 |
| Sodium/hydrogen exchanger 1 | 6548 | SLC9A1 | 13 |
| Solute carrier family 12 member 9 | 56996 | SLC12A9 | 13 |
| Solute carrier family 2, facilitated glucose transporter member 1 | 6513 | SLC2A1 | 12 |
| Sodium- and chloride-dependent taurine transporter | 6533 | SLC6A6 | 12 |
| Solute carrier organic anion transporter family member 4A1 | 28231 | SLCO4A1 | 12 |
| Solute carrier family 23 member 2 | 9962 | SLC23A2 | 12 |
| Solute carrier organic anion transporter family member 3A1 | 28232 | SLCO3A1 | 12 |
| Prestin | 375611 | SLC26A5 | 11 |
| Equilibrative nucleoside transporter 2 | 3177 | SLC29A2 | 11 |
| Equilibrative nucleoside transporter 1 | 2030 | SLC29A1 | 11 |
| Sodium-coupled neutral amino acid transporter 1 | 81539 | SLC38A1 | 11 |
| Sodium bicarbonate cotransporter 3 | 9497 | SLC4A7 | 11 |
| Urea transporter 1 | 6563 | SLC14A1 | 10 |
| Transmembrane and coiled-coil domain-containing protein 3 | 55002 | TMCO3 | 10 |
| Signal peptide peptidase-like 2A | 84888 | SPPL2A | 9 |
| Transmembrane 9 superfamily member 3 | 56889 | TM9SF3 | 9 |
| Anoctamin-9 | 338440 | ANO9 | 8 |
| Sodium/potassium-transporting ATPase subunit alpha-1 | 476 | ATP1A1 | 8 |
| Sodium/potassium-transporting ATPase subunit alpha-3 | 478 | ATP1A3 | 8 |
| Anoctamin-6 | 196527 | ANO6 | 8 |
| V-type proton ATPase 116 kDa subunit a isoform 2 | 23545 | ATP6V0A2 | 8 |
| Putative P2Y purinoceptor 10 | 27334 | P2RY10 | 7 |
| G-protein coupled receptor 39 | 2863 | GPR39 | 7 |
| Sphingosine 1-phosphate receptor 2 | 9294 | S1PR2 | 7 |
| Latrophilin-2 | 23266 | LPHN2 | 7 |
| Beta-2 adrenergic receptor | 154 | ADRB2 | 7 |
| Alpha-2C adrenergic receptor | 152 | ADRA2C | 7 |
| Thromboxane A2 receptor | 6915 | TBXA2R | 7 |
| Platelet-activating factor receptor | 5724 | PTAFR | 7 |
| Proteinase-activated receptor 1 | 2149 | F2R | 7 |
| Neuropeptide Y receptor type 1 | 4886 | NPY1R | 7 |
| Type-1 angiotensin II receptor | 185 | AGTR1 | 7 |
| Neurotensin receptor type 1 | 4923 | NTSR1 | 7 |
| Cannabinoid receptor 2 | 1269 | CNR2 | 7 |
| Prostaglandin E2 receptor EP2 subtype | 5732 | PTGER2 | 7 |
| Calcitonin gene-related peptide type 1 receptor | 10203 | CALCRL | 7 |
| Protein GPR107 | 57720 | GPR107 | 7 |
| G-protein coupled receptor 126 | 57211 | GPR126 | 7 |
| P2Y purinoceptor 8 | 286530 | P2RY8 | 7 |
| Probable G-protein coupled receptor 125 | 166647 | GPR125 | 7 |
| Transmembrane protein 87A | 25963 | TMEM87A | 7 |

TABLE 1-continued

Exemplary Human Multi-Pass Integral Membrane Proteins

| Protein Name | ENTREZ_gene_ID | ENTREZ gene symbol | # predicted TM domains |
|---|---|---|---|
| Mas-related G-protein coupled receptor member F | 116535 | MRGPRF | 7 |
| Transmembrane protein 87B | 84910 | TMEM87B | 7 |
| Proteinase-activated receptor 4 | 9002 | F2RL3 | 7 |
| Smoothened homolog | 6608 | SMO | 7 |
| EGF-like module-containing mucin-like hormone receptor-like 3 | 84658 | EMR3 | 7 |
| Neuromedin-U receptor 1 | 10316 | NMUR1 | 7 |
| EGF, latrophilin and seven transmembrane domain-containing protein 1 | 64123 | ELTD1 | 7 |
| Transmembrane protein 8A | 58986 | TMEM8A | 7 |
| Cadherin EGF LAG seven-pass G-type receptor 2 | 1952 | CELSR2 | 7 |
| Cadherin EGF LAG seven-pass G-type receptor 1 | 9620 | CELSR1 | 7 |
| Cadherin EGF LAG seven-pass G-type receptor 3 | 1951 | CELSR3 | 7 |
| Cysteinyl leukotriene receptor 1 | 10800 | CYSLTR1 | 7 |
| G-protein coupled receptor 56 | 9289 | GPR56 | 7 |
| Lipid phosphate phosphohydrolase 1 | 8611 | PPAP2A | 6 |
| Potassium voltage-gated channel subfamily A member 3 | 3738 | KCNA3 | 6 |
| Zinc transporter ZIP6 | 25800 | SLC39A6 | 6 |
| Zinc transporter ZIP14 | 23516 | SLC39A14 | 6 |
| P2Y purinoceptor 11 | 5032 | P2RY11 | 6 |
| Zinc transporter ZIP10 | 57181 | SLC39A10 | 6 |
| Cytochrome b-245 heavy chain | 1536 | CYBB | 5 |
| Prominin-2 | 150696 | PROM2 | 5 |
| Protein tweety homolog 2 | 94015 | TTYH2 | 5 |
| Protein tweety homolog 3 | 80727 | TTYH3 | 5 |
| Gamma-aminobutyric acid receptor subunit beta-3 | 2562 | GABRB3 | 4 |
| Glutamate receptor, ionotropic kainate 3 | 2899 | GRIK3 | 4 |
| Neuronal membrane glycoprotein M6-b | 2824 | GPM6B | 4 |
| Metal transporter CNNM4 | 26504 | CNNM4 | 4 |
| Metal transporter CNNM3 | 26505 | CNNM3 | 3 |
| Discoidin, CUB and LCCL domain-containing protein 2 | 131566 | DCBLD2 | 3 |
| Transmembrane protein 131-like | 23240 | KIAA0922 | 2 |
| Leucine-rich repeat transmembrane protein FLRT2 | 23768 | FLRT2 | 2 |
| Attractin | 8455 | ATRN | 2 |
| Receptor-type tyrosine-protein phosphatase gamma | 5793 | PTPRG | 2 |
| Interferon alpha/beta receptor 2 | 3455 | IFNAR2 | 2 |
| Ephrin type-A receptor 5 | 2044 | EPHA5 | 2 |
| Tyrosine-protein kinase transmembrane receptor ROR1 | 4919 | ROR1 | 2 |
| Tomoregulin-1 | 8577 | TMEFF1 | 2 |
| P2X purinoceptor 7 | 5027 | P2RX7 | 2 |
| TM2 domain-containing protein 3 | 80213 | TM2D3 | 2 |
| TM2 domain-containing protein 1 | 83941 | TM2D1 | 2 |
| G-protein coupled receptor 64 | 10149 | GPR64 | 8 |
| Psychosine receptor | 8477 | GPR65 | 6 |
| Large neutral amino acids transporter small subunit 1 | 8140 | SLC7A5 | 12 |
| Sphingosine 1-phosphate receptor 3 | 1903 | S1PR3 | 7 |
| Solute carrier organic anion transporter family member 2A1 | 6578 | SLCO2A1 | 12 |
| Type-2 angiotensin II receptor | 186 | AGTR2 | 7 |
| UPF0513 transmembrane protein | 79583 | UNQ870/PRO1886 | 2 |
| Lipid phosphate phosphohydrolase 3 | 8613 | PPAP2B | 5 |
| Blood vessel epicardial substance | 11149 | BVES | 3 |
| Sodium/potassium/calcium exchanger 6 | 80024 | SLC24A6 | 13 |
| 5-hydroxytryptamine receptor 2B | 3357 | HTR2B | 7 |
| Mucolipin-1 | 57192 | MCOLN1 | 6 |
| Cadherin-8 | 1006 | CDH8 | 2 |
| Adenosine receptor A1 | 134 | ADORA1 | 7 |
| Probable G-protein coupled receptor 110 | 266977 | GPR110 | 7 |
| Chemokine receptor-like 1 | 1240 | CMKLR1 | 7 |
| Proton-coupled folate transporter | 113235 | SLC46A1 | 11 |
| Sphingosine 1-phosphate receptor 4 | 8698 | S1PR4 | 7 |
| Protein FAM171A2 | 284069 | FAM171A2 | 2 |
| Alpha-2A adrenergic receptor | 150 | ADRA2A | 7 |
| C-X-C chemokine receptor type 7 | 57007 | CXCR7 | 7 |

TABLE 1-continued

Exemplary Human Multi-Pass Integral Membrane Proteins

| Protein Name | ENTREZ_gene_ID | ENTREZ gene symbol | # predicted TM domains |
|---|---|---|---|
| Apelin receptor | 187 | APLNR | 7 |
| Probable G-protein coupled receptor 116 | 221395 | GPR116 | 7 |
| Metalloreductase STEAP4 | 79689 | STEAP4 | 6 |
| Solute carrier organic anion transporter family member 4C1 | 353189 | SLCO4C1 | 12 |
| ATP-binding cassette sub-family A member 8 | 10351 | ABCA8 | 14 |
| Vasoactive intestinal polypeptide receptor 1 | 7433 | VIPR1 | 7 |
| SID1 transmembrane family member 2 | 51092 | SIDT2 | 11 |
| Equilibrative nucleoside transporter 4 | 222962 | SLC29A4 | 10 |
| Succinate receptor 1 | 56670 | SUCNR1 | 7 |
| Metal transporter CNNM2 | 54805 | CNNM2 | 4 |
| Probable palmitoyltransferase ZDHHC5 | 25921 | ZDHHC5 | 4 |
| Solute carrier family 22 member 16 | 85413 | SLC22A16 | 12 |
| Leukotriene B4 receptor 1 | 1241 | LTB4R | 7 |
| Pannexin-1 | 24145 | PANX1 | 4 |
| Sodium-dependent glucose transporter 1 | 91749 | NAGLT1 | 11 |
| Sodium/calcium exchanger 1 | 6546 | SLC8A1 | 10 |
| Neuronal acetylcholine receptor subunit alpha-3 | 1136 | CHRNA3 | 4 |
| Retinoic acid-induced protein 3 | 9052 | GPRC5A | 7 |
| Lysophosphatidic acid receptor 5 | 57121 | LPAR5 | 7 |
| Probable G-protein coupled receptor 132 | 29933 | GPR132 | 7 |
| Sphingosine 1-phosphate receptor 5 | 53637 | S1PR5 | 7 |
| Endothelin-1 receptor | 1909 | EDNRA | 7 |
| Probable G-protein coupled receptor 124 | 25960 | GPR124 | 7 |
| Solute carrier family 12 member 7 | 10723 | SLC12A7 | 12 |
| Thyrotropin receptor | 7253 | TSHR | 7 |
| Transient receptor potential cation channel subfamily V member 2 | 51393 | TRPV2 | 6 |
| Glutamate receptor delta-1 subunit | 2894 | GRID1 | 4 |
| Gamma-aminobutyric acid receptor subunit alpha-2 | 2555 | GABRA2 | 4 |
| Sphingosine 1-phosphate receptor 1 | 1901 | S1PR1 | 7 |
| Prostaglandin E2 receptor EP3 subtype | 5733 | PTGER3 | 7 |
| Probable G-protein coupled receptor 174 | 84636 | GPR174 | 7 |
| Glutamate receptor 2 | 2891 | GRIA2 | 3 |
| Amiloride-sensitive sodium channel subunit delta | 6339 | SCNN1D | 2 |
| 5-hydroxytryptamine receptor 1D | 3352 | HTR1D | 7 |
| Goliath homolog | 55819 | RNF130 | 2 |
| ATP-binding cassette sub-family A member 7 | 10347 | ABCA7 | 11 |
| Prostacyclin receptor | 5739 | PTGIR | 7 |
| Probable G-protein coupled receptor 176 | 11245 | GPR176 | 7 |
| Thyrotropin-releasing hormone receptor | 7201 | TRHR | 7 |
| Claudin-12 | 9069 | CLDN12 | 4 |
| Protein FAM38A | 9780 | FAM38A | 29 |
| Niemann-Pick C1 protein | 4864 | NPC1 | 13 |
| Synaptic vesicle glycoprotein 2A | 9900 | SV2A | 12 |
| Signal peptide peptidase-like 2B | 56928 | SPPL2B | 9 |
| Rhomboid family member 2 | 79651 | RHBDF2 | 7 |
| Immunoglobulin superfamily member 1 | 3547 | IGSF1 | 4 |
| Dolichyl-diphosphooligosaccharide--protein glycosyltransferase subunit 2 | 6185 | RPN2 | 3 |
| Transmembrane emp24 domain-containing protein 9 | 54732 | TMED9 | 2 |
| Steryl-sulfatase | 412 | STS | 2 |
| Transmembrane 9 superfamily member 1 | 10548 | TM9SF1 | 9 |
| Melanoma inhibitory activity protein 3 | 375056 | MIA3 | 2 |
| Arylsulfatase F | 416 | ARSF | 2 |
| Solute carrier family 2, facilitated glucose transporter member 4 | 6517 | SLC2A4 | 12 |
| Anoctamin-5 | 203859 | ANO5 | 8 |
| Nicalin | 56926 | NCLN | 2 |

In certain aspects, the multi-pass IMP is a GPCR, e.g., FZD4 or CXCR4. In certain aspects the multi-pass IMP is CD20.

Polynucleotides Encoding IMP Fusion Proteins for Expression on Poxvirus EEV

This disclosure provides an isolated polynucleotide for expression of an integral membrane protein or fragment thereof in a conformationally-intact form in the context of a biological membrane, as a fusion with a protein or fragment thereof specific for vaccinia virus EEV. By "conformationally intact" is meant that the protein appears, or is displayed, in a native or close to native conformation in the context of a biological lipid bilayer membrane, much as the protein would appear in its native state.

Figure 1B:
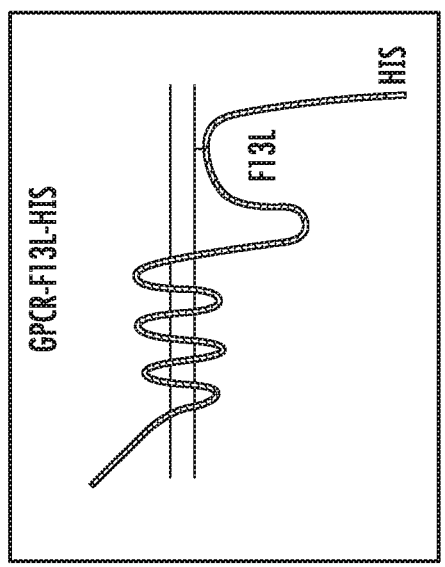

In one aspect, the disclosure provides an isolated polynucleotide that includes a first nucleic acid fragment that encodes an integral membrane protein (IMP) or fragment thereof, e.g., a multi-pass IMP, where the IMP or fragment thereof comprises at least one extra-membrane region, at least one transmembrane domain and at least one intra-membrane region, and where a portion of the first nucleic acid fragment encoding at least one intra-membrane region is situated at the 5' or 3' end of the first nucleic acid fragment; and a second nucleic acid fragment that encodes a vaccinia virus F13L protein (SEQ ID NO: 1) or functional fragment thereof, where the second nucleic acid fragment is fused in frame to a portion of the first nucleic acid fragment that encodes an intra-membrane region of the IMP. The first nucleic acid fragment and the second nucleic acid fragment can, in some instances, we separated by a nucleic acid encoding a linker or other spacer. The polynucleotide can further include a poxvirus promoter operably associated with the first and second nucleic acid fragments, allowing expression of the polynucleotide in the cytoplasm of a poxvirus-infected cell. According to this aspect, a poxvirus-infected cell that contains the polynucleotide can express an IMP-F13L fusion protein as part of the outer envelope membrane of an extracellular enveloped virion (EEV). Schematic diagrams showing expression of an IMP as a fusion with F13L are shown in FIG. 1B and FIG. 1C.

In certain aspects, the IMP or fragment thereof can be a multi-pass membrane protein comprising at least two, at least three, at least four, at least five, at least six, at least seven, at least eight, at least nine, at least ten, at least eleven, at least twelve, or even more transmembrane (TM) domains, such as those listed in Table 1.

Where the IMP has an odd number of TM domains, one end of the IMP, either the N-terminus or the C-terminus, will be naturally situated on the extra-membrane side of the biological membrane and the other end of the IMP will be situated on the intra-membrane side of the IMP. Since the F13L protein is wholly-internal to the outer membrane of poxvirus EEVs, the end of the IMP, the N-terminus or the C-terminus that is situated internal to the membrane can be fused to F13L. Thus for an IMP such as a typical 7-TM domain GPCR in which the N-terminus of the protein is extra-membrane and the C-terminus is intra-membrane, the N-terminus of F13L can be fused to the C-terminus of the GPCR as shown in FIG. 1B. Accordingly, a polynucleotide as above is provided where the first nucleic acid fragment encodes an IMP with an odd number of transmembrane domains, where the 5' end of the first nucleic acid fragment encodes the extra-membrane region, and the 3' end of the first nucleic acid fragment encodes the intra-membrane region of the IMP, the latter being fused to the 5' end of the nucleic acid fragment encoding F13L or a fragment thereof.

In an exemplary polynucleotide of this type, the first polynucleotide can encode the human frizzled-4 protein (FZD4), or a fragment thereof, a target for immunotherapy of certain human cancers, fused to the N-terminus of F13L. Accordingly, a polynucleotide which encodes an FZD4-F13L fusion protein is provided. An exemplary polynucleotide according to this aspect encodes the mature fusion protein, amino acids 20 to 892 of SEQ ID NO: 2, as shown below. The polynucleotide can further encode a signal peptide, e.g., the signal peptide of FZD4, amino acids 1 to 19 of SEQ ID NO: 2.

FZD(FL)-F13L
(SEQ ID NO: 2)
MGWSCIILFLVATATGAHSFGDEEERRCDPIRISMCQNLGYNVTK

MPNLVGHELQTDAELQLTTFTPLIQYGCSSQLQFFLCSVYVPMCT

EKINIPIGPCGGMCLSVKRRCEPVLKEFGFAWPESLNCSKFPPQN

DHNHMCMEGPGDEEVPLPHKTPIQPGEECHSVGTNSDQYIWVKRS

LNCVLKCGYDAGLYSRSAKEFTDIWMAVWASLCFISTAFTVLTFL

IDSSRFSYPERPIIFLSMCYNIYSIAYIVRLTVGRERISCDFEEA

AEPVLIQEGLKNTGCAIIFLLMYFFGMASSIWWVILTLTWFLAAG

LKWGHEAIEMHSSYFHIAAWAIPAVKTIVILIMRLVDADELTGLC

YVGNQNLDALTGFVVAPLFTYLVIGTLFIAAGLVALFKIRSNLQK

DGTKTDKLERLMVKIGVFSVLYTVPATCVIACYFYEISNWALFRY

SADDSNMAVEMLKIFMSLLVGITSGMWIWSAKTLHTWQKCSNRLV

NSGKVKREKRGNGWVKPGKGSETVV*MWPFASVPAGAKCRLVETLP*

*ENMDFRSDHLTTFECFNEIITLAKKYIYIASFCCNPLSTTRGALI*

*FDKLKEASEKGIKIIVLLDERGKRNLGELQSHCPDINFITVNIDK*

*KNNVGLLLGCFWVSDDERCYVGNASFTGGSIHTIKTLGVYSDYPP*

*LATDLRRRFDTFKAFNSAKNSWLNLCSAACCLPVSTAYHIKNPIG*

*GVFFTDSPEHLLGYSRDLDTDVVIDKLKSAKTSIDIEHLAIVPTT*

*RVDGNSYYWPDIYNSIIEAAINRGVKIRLLVGNWDKNDVYSMATA*

*RSLDALCVQNDLSVKVFTIQNNTKLLIVDDEYVHITSANFDGTHY*

*QNHGFVSFNSIDKQLVSEAKKIFERDWVSSHSKSLKI*

Single Underline—leader peptide (amino acids 1-19)
Bold—human Fzd4 (amino acids 20-520)
Italics—F13L (amino acids 521-892)

In another exemplary polynucleotide of this type, the first polynucleotide can encode A CXC chemokine receptor, or a fragment thereof, fused to the N-terminus of F13L. CXC chemokine receptors are likewise targets for immunotherapy of certain human cancers. An exemplary CXC chemokine receptor is CXCR4, or a fragment thereof. Accordingly, a polynucleotide which encodes a CXC chemokine receptor-F13L fusion protein, e.g., a CXCR4-F13L fusion protein is provided. An exemplary polynucleotide according to this aspect encodes SEQ ID NO: 3, as shown below.

CXCR4-F13L
(SEQ ID NO: 3)
MAIPLPLLQIYTSDNYTEEMGSGDYDSMKEPCFREENANFNKIFL

PTIYSIIFLTGIVGNGLVILVMGYQKKLRSMTDKYRLHLSVADLL

FVITLPFWAVDAVANWYFGNFLCKAVHVIYTVNLYSSVLILAFIS

LDRYLAIVHATNSQRPRKLLAEKVVYVGVWIPALLLTIPDFIFAN

VSEADDRYICDRFYPNDLWVVVFQFQHIMVGLILPGIVILSCYCI

IISKLSHSKGHQKRKALKTTVILILAFFACWLPYYIGISIDSFIL

LEIIKQGCEFENTVHKWISITEALAFFHCCLNPILYAFLGAKFKT

SAQHALTSVSRGSSLKILSKGKRGGHSSVSTESESSSFHSS*MWPF*

*ASVPAGAKCRLVETLPENMDFRSDHLTTFECFNEIITLAKKYIYI*

-continued
```
ASFCCNPLSTTRGALIFDKLKEASEKGIKIIVLLDERGKRNLGEL

QSHCPDINFITVNIDKKNNVGLLLGCFWVSDDERCYVGNASFTGG

SIHTIKTLGVYSDYPPLATDLRRRFDTFKAFNSAKNSWLNLCSAA

CCLPVSTAYHIKNPIGGVFFTDSPEHLLGYSRDLDTDVVIDKLKS

AKTSIDIEHLAIVPTTRVDGNSYYWPDIYNSIIEAAINRGVKIRL

LVGNWDKNDVYSMATARSLDALCVQNDLSVKVFTIQNNTKLLIVD

DEYVHITSANFDGTHYQNHGFVSFNSIDKQLVSEAKKIFERDWVS

SHSKSLKI
```

Bold—human CXCR4 (amino acids 1-356)
Italics—F13L (amino acids 357-728)

As will be evident to a person of ordinary skill in the art, a multi-pass membrane protein having an even number of transmembrane domains will be inserted into a biological membrane such that its N-terminus and its C-terminus are on the same side of the membrane, either on the extra-membrane side of the membrane, or on the intra-membrane side of the membrane. Since the F13L protein is situated entirely on the intra-membrane side of poxvirus EEVs, formation of an IMP-F13L fusion protein properly embedded in the membrane would need at least one of the N-terminus or the C-terminus of the IMP or fragment thereof to be internal to the membrane. Where the IMP has an even number of TM domains and both are situated internally, the F13L protein can be fused either to the N-terminus of the IMP or to the C-terminus of the IMP. If the full-length IMP is situated such that both the N- and C-terminus are extra-membrane, a fragment of the IMP having an odd number of TM domains can be fused to F13L.

Accordingly, the disclosure provides a polynucleotide as described above that encodes an IMP with an even number of transmembrane domains, where both the 5' and 3' ends of the first nucleic acid fragment encode intra-membrane regions. In certain aspects the 3' end of the nucleic acid fragment encoding F13L can be fused to the 5' end of the nucleic acid fragment encoding the IMP, in certain aspects the 5' end of the nucleic acid fragment encoding F13L can be fused to the 3' end of the nucleic acid fragment encoding the IMP.

An exemplary IMP of this type is human CD20, a 4-TM domain IMP expressed on human B cells, which is a target for immunotherapy of B cell leukemias, lymphomas, and myelomas. A diagram of a CD20-F13L fusion protein in which the C-terminus of CD20 is fused to the N-terminus of F13L is shown in FIG. 1C. Accordingly, a polynucleotide which encodes a CD20-F13L fusion protein is provided. An exemplary polynucleotide according to this aspect encodes SEQ ID NO: 4, as shown below.

CD20-F13L
(Seq ID NO: 4)

MATPRNSVNGTFPAEPMKGPIAMQSGPKPLFRRMSSLVGPTQSFF

MRESKTLGAVQIMNGLFHIALGGLLMIPAGIYAPICVTVWYPLWG

GIMYIISGSLLAATEKNSRKCLVKGKMIMNSLSLFAAISGMILSI

MDILNIKISHFLKMESLNFIRAHTPYINIYNCEPANPSEKNSPST

QYCYSIQSLFLGILSVMLIFAFFQELVIAGIVENEWKRTCSRPKS

NIVLLSAEEKKEQTIEIKEEVVGLTETSSQPKNEEDIEIIPIQEE

-continued

EEEETETNFPEPPQDQESSPIENDSSP*MWPFASVPAGAKCRLVET*

*LPENMDFRSDHLTTFECFNEIITLAKKYIYIASFCCNPLSTTRGA*

*LIFDKLKEASEKGIKIIVLLDERGKRNLGELQSHCPDINFITVNI*

*DKKNNVGLLLGCFWVSDDERCYVGNASFTGGSIHTIKTLGVYSDY*

*PPLATDLRRRFDTFKAFNSAKNSWLNLCSAACCLPVSTAYHIKNP*

*IGGVFFTDSPEHLLGYSRDLDTDVVIDKLKSAKTSIDIEHLAIVP*

*TTRVDGNSYYWPDIYNSIIEAAINRGVKIRLLVGNWDKNDVYSMA*

*TARSLDALCVQNDLSVKVFTIQNNTKLLIVDDEYVHITSANFDGT*

*HYQNHGFVSFNSIDKQLVSEAKKIFERDWVSSHSKSLKI*

Bold—human CD20 (MS4A1) (amino acids 1-298)
Italics—F13L (amino acids 299-669)

In polynucleotides as provided above, the first and second nucleic acid fragments can be directly fused, or alternatively they can be separated by a nucleic acid fragment encoding a linker or spacer or other polypeptide fragment. In certain aspects, a polynucleotide as provided above can further include a third nucleic acid fragment that encodes a heterologous peptide polypeptide, either between the first and second nucleic acid fragments, or on either side. The heterologous peptide can be, for example, a linker sequence, an amino acid tag or label, or a peptide or polypeptide sequence that facilitates purification. In certain aspects the heterologous peptide is a 6-histidine tag fused, e.g., to the C-terminus of the fusion protein.

In certain aspects, a polynucleotide as provided herein is operably associated with a poxvirus promoter. Suitable promoters are described elsewhere herein. In certain aspects the promoter is a poxvirus p7.5 promoter or a poxvirus H5 promoter.

A polynucleotide as provided herein can be or can be part of, a poxvirus genome, where the poxvirus genome, upon introduction into a suitable permissive host cell, can produce infectious EEV that display the IMP-F13L fusion protein on their surface. In certain aspects the poxvirus genome is a vaccinia virus genome, e.g., a vaccinia virus WR genome or an MVA genome. A poxvirus genome comprising a polynucleotide as described can be produced by standard molecular biological and virology techniques, for example by using tri-molecular recombination as described herein. A poxvirus genome as provided herein can be introduced into permissive cells as part of a recombinant poxvirus, or as naked DNA accompanied by suitable helper viruses, e.g., fowlpox virus. The disclosure further provides a recombinant poxvirus, e.g., a recombinant vaccinia virus comprising the provided poxvirus genome.

IMP-EEV Fusion Proteins, Recombinant Poxvirus EEVs, and Methods of Making

This disclosure further provides an IMP-F13L fusion protein such as those encoded by the polynucleotides described above. Moreover, the IMP-F13L fusion protein can be expressed on the surface of a recombinant poxvirus EEV, e.g., a recombinant vaccinia virus EEV. A recombinant poxvirus EEV, e.g., a recombinant vaccinia virus EEV comprising the provided fusion protein is provided by the disclosure. A recombinant poxvirus EEV can be produced by a method that includes infecting a host cell permissive for vaccinia virus infectivity with a vaccinia virus comprising a poxvirus genome as provided above, and recovering EEV released from the infected host cell. Accordingly, an IMP-F13L fusion protein encoded by a polynucleotide as described above, is provided.

Moreover the disclosure provides fusion proteins comprising an IMP or fragment thereof, which can be a multi-pass IMP, and single pass IMP, or even just the extracellular domain (ECD) of the IMP, fused to a poxvirus protein, e.g., a vaccinia virus protein, specific for EEV, such as F13L, A56R, B5R, 33R, A34R, or A36R, an "IMP-EEV fusion protein." Exemplary ECD fusion proteins are described below. An IMP-EEV fusion protein as provided herein can display the IMP, e.g., a multi-pass IMP, single-pass IMP or ECD of an IMP, in a conformationally intact form on the surface of poxvirus EEV. For use in screening antibody display libraries for antigen binding domains that specifically bind to a target IMP, display of IMPs on the surface of poxvirus EEV offers many advantages over displaying IMPs on the surface of recombinant cells, e.g., CHO cells, as is typical. For example the IMP can be expressed at higher density on EEV than on cells. Moreover, EEV express only about six different poxvirus proteins on their surface (e.g., F13L, A56R, B5R, 33R, A34R, and A36R) as opposed to hundreds that might be expressed on the surface of cells. Finally, inactivated EEV expressing IMP-F13L fusion proteins as provided herein can be attached to solid supports, offering convenience in library screening.

Accordingly, this disclosure provides a method to display an integral membrane protein (IMP) or fragment thereof in a native conformation for use, e.g., in screening antibody display libraries for antigen binding domains specific for the IMP. The method includes: infecting host cells permissive for poxvirus infectivity with a recombinant poxvirus that expresses the IMP or fragment thereof as a fusion protein with poxvirus EEV-specific protein or membrane-associated fragment thereof, where EEV produced by the infected host cell comprise the IMP as part of the EEV outer envelope membrane; and recovering EEV released from the host cell. IMP. In certain aspects, the EEV-specific protein or fragment thereof can be the vaccinia virus A33R protein, A34R protein, A56R protein, B5R protein, A36R protein, F13L protein, any membrane-associated fragment thereof, or any combination thereof.

In certain aspects, the EEV-specific protein is F13L (SEQ ID NO: 1) or a functional fragment thereof, and the fusion protein can be one expressed by a polynucleotide as provided above, e.g., where the IMP is a multi-pass membrane protein comprising at least two, at least three, at least four, at least five, at least six or at least seven transmembrane domains.

In certain aspects, the membrane-associated EEV specific protein fragment includes the stalk, transmembrane, and intra-membrane domains of the vaccinia virus A56R protein, a fragment comprising, consisting of, or consisting essentially of amino acids 108 to 314 of SEQ ID NO: 5. One of several exemplary fusion partners includes the ECD of human FZD4, shown in bold in SEQ ID NO: 6 below. According to this exemplary aspect the disclosure provides a method to display a conformationally intact fragment of human FZD4 on the surface of a poxvirus EEV comprising infecting host cells permissive for poxvirus infectivity with a recombinant poxvirus encoding a fusion protein comprising amino acids 20 to 370 of SEQ ID NO: 6. In certain aspects the fusion protein can further comprise a signal peptide, e.g., amino acids 1 to 19 of SEQ ID NO: 6.

FZD-ECD-A56R
(Seq ID NO: 6)
MGWSCIILFLVATATGAHSFGDEEERRCDPIRISMCQNLGYNVTK

MPNLVGHELQTDAELQLTTFTPLIQYGCSSQLQFFLCSVYVPMCT

EKINIPIGPCGGMCLSVKRRCEPVLKEFGFAWPESLNCSKFPPQN

DHNHMCMEGPGDEEVPLPHKTPIQPGEETSTTNDTDKVDYEEYST

ELIVNTDSESTIDIILSGSTHSPETSSKKPDYIDNSNCSSVFEIA

TPEPITDNVEDHTDTVTYTSDSINTVSASSGESTTDETPEPITDK

EDHTVTDTVSYTTVSTSSGIVTTKSTTDDADLYDTYNDNDTVPPT

TVGGSTTSISNYKTKDFVEIFGITALIILSAVAIFCITYYIYNKR

SRKYKTENKV.

Single Underline—leader peptide (amino acids 1-19)
Bold—human FZD4 extracellular domain (amino acids 20-163)
Italics—A56R stalk, transmembrane, and intra-membrane (amino acids 164 to 370)

Another exemplary fusion partner includes the ECD of human ErbB2 (Her2), shown in bold in SEQ ID NO: 7 below. According to this exemplary aspect the disclosure provides a method to display a conformationally intact fragment of human Her2 on the surface of a poxvirus EEV comprising infecting host cells permissive for poxvirus infectivity with a recombinant poxvirus encoding a fusion protein comprising amino acids 20 to 855 of SEQ ID NO: 7. In certain aspects the fusion protein can further comprise a signal peptide, e.g., amino acids 1 to 19 of SEQ ID NO: 7.

Her2-A56R
(SEQ ID NO: 7)
MGWSCIILFLVATATGAHSSTQVCTGTDMKLRLPASPETHLDMLR

HLYQGCQVVQGNLELTYLPTNASLSFLQDIQEVQGYVLIAHNQVR

QVPLQRLRIVRGTQLFEDNYALAVLDNGDPLNNTTPVTGASPGGL

RELQLRSLTEILKGGVLIQRNPQLCYQDTILWKDIFHKNNQLALT

LIDTNRSRACHPCSPMCKGSRCWGESSEDCQSLTRTVCAGGCARC

KGPLPTDCCHEQCAAGCTGPKHSDCLACLHFNHSGICELHCPALV

TYNTDTFESMPNPEGRYTFGASCVTACPYNYLSTDVGSCTLVCPL

HNQEVTAEDGTQRCEKCSKPCARVCYGLGMEHLREVRAVTSANIQ

EFAGCKKIFGSLAFLPESFDGDPASNTAPLQPEQLQVFETLEEIT

GYLYISAWPDSLPDLSVFQNLQVIRGRILHNGAYSLTLQGLGISW

LGLRSLRELGSGLALIHHNTHLCFVHTVPWDQLFRNPHQALLHTA

NRPEDECVGEGLACHQLCARGHCWGPGPTQCVNCSQFLRGQECVE

ECRVLQGLPREYVNARHCLPCHPECQPQNGSVTCFGPEADQCVAC

AHYKDPPFCVARCPSGVKPDLSYMPIWKFPDEEGACQPCPINCTH

SCVDLDDKGCPAEQRASPTSTTNDTDKVDYEEYSTELIVNTDSES

TIDIILSGSTHSPETSSKKPDYIDNSNCSSVFEIATPERITDNVE

DHTDTVTYTSDSINTVSASSGESTTDETPEPITDKEDHTVTDTVS

YTTVSTSSGIVTTKSTTDDADLYDTYNDNDTVPPTTVGGSTTSIS

NYKTKDFVEIFGITALIILSAVAIFCITYYIYNKRSRKYKTENKV.

Single Underline—leader peptide (amino acids 1-19)
Bold—human ERBB2 (HER2) extracellular domain (amino acids 20-648)
Italics—A56R stalk, transmembrane, and intra-membrane (amino acids 649 to 855)

Another exemplary fusion partner includes the ECD of human CD100 (Semaphorin 4D), shown in bold in SEQ ID NO: 8 below. According to this exemplary aspect the disclosure provides a method to display a conformationally intact fragment of human CD100 on the surface of a poxvirus EEV comprising infecting host cells permissive for poxvirus infectivity with a recombinant poxvirus encoding a fusion protein comprising amino acids 20 to 935 of SEQ ID NO: 8. In certain aspects the fusion protein can further comprise a signal peptide, e.g., amino acids 1 to 19 of SEQ ID NO: 8.

CD100-A56R (SEQ ID NO: 8)

MGWSCIILFLVATATGAHSFAPIPRITWEHREVHLVQFHE

PDIYNYSALLLSEDKDTLYIGAREAVFAVNALNISEKQHE

VYWKVSEDKKAKCAEKGKSKQTECLNYIRVLQPLSATS

LYVCGTNAFQPACDHLNLTSFKFLGKNEDGKGRCPFDP

AHSYTSVMVDGELYSGTSYNFLGSEPIISRNSSHSPLRTEY

AIPWLNEPSFVFADVIRKSPDSPDGEDDRVYFFFTEVSVE

YEFVFRVLIPRIARVCKGDQGGLRTLQKKWTSFLKARLI

CSRPDSGLVFNVLRDVFVLRSPGLKVPVFYALFTPQLNN

VGLSAVCAYNLSTAEEVFSHGKYMQSTTVEQSHTKWVR

YNGPVPKPRPGACIDSEARAANYTSSLNLPDKTLQFVKD

HPLMDDSVTPIDNRPRLIKKDVNYTQIVVDRTQALDGTV

YDVMFVSTDRGALHKAISLEHAVHIIEETQLFQDFEPVQ

TLLLSSKKGNRFVYAGSNSGVVQAPLAFCGKHGTCEDC

VLARDPYCAWSPPTATCVALHQTESPSRGLIQEMSGDAS

VCPDKSKGSYRQHFFKHGGTAELKCSQKSNLARVFWKF

QNGVLKAESPKYGLMGRKNLLIFNLSEGDSGVYQCLSE

ERVKNKTVFQVVAKHVLEVKVVPKPVVAPTLSVVQTEG

SRIATKVLVASTQGSSPPTPAVQATSSGAITLPPKPAPTGT

SCEPKIVINTVPQLHSEKTMYLKSSD_TSTTNDTDKVDYEEYS_

_TELIVNTDSESTIDIILSGSTHSPETSSKKPDYIDNSNCSSVFEIATP_

_EPITDNVEDHTDTVTYTSDSINTVSASSGESTTDETPEPITDKED_

_HTVTDTVSYTTVSTSSGIVTTKSTTDDADLYDTYNDNDTVPPTTV_

_GGSTTSISNYKTKDFVEIFGITALIILSAVAIFCITYYIYNKRSRKYK_

_TENKV_.

Single Underline—leader peptide (amino acids 1-19)
Bold—human CD100 extracellular domain (amino acids 20-728)
Italics—A56R stalk, transmembrane, and intra-membrane (amino acids 729 to 935)

In certain aspects, the membrane-associated EEV specific protein fragment includes the transmembrane and intra-membrane domains of the vaccinia virus B5R protein, a fragment comprising, consisting of, or consisting essentially of amino acids 276 to 317 of SEQ ID NO: 9. In certain aspects, the membrane-associated EEV specific protein fragment includes the stalk, transmembrane, and intra-membrane domains of the vaccinia virus B5R protein, a fragment comprising, consisting of, or consisting essentially of amino acids 238 to 317 of SEQ ID NO: 9.

SEQ ID NO: 9: WRB5R protein
MKTISVVTLLCVLPAVVYSTCTVPTMNNAKLTSTETSFNDK

QKVTFTCDQGYHSSDPNAVCETDKWKYENPCKKMCTVSD

YISELYNKPLYEVNSTMTLSCNGETKYFRCEEKNGNTSWND

TVTCPNAECQPLQLEHGSCQPVKEKYSFGEYMTINCDVGYE

VIGASYISCTANSWNVIPSCQQKCDMPSLSNGLISGSTFSIGG

VIHLSCKSGFTLTGSPSSTCIDGKWNPVLPICVRTNEEFDPVD

DGPDDETDLSKLSKDVVQYEQEIESLEATYHIIIVALTIMGVI

FLISVIVLVCSCDKNNDQYKFHKLLP

In certain exemplary aspects the IMP fusion partner for the B5R fragment comprises the extracellular domain of human FZD4, shown in bold in SEQ ID NO: 10 and SEQ ID NO: 11 below. According to this exemplary aspect the disclosure provides a method to display a conformationally intact fragment of human FZD4 on the surface of a poxvirus EEV comprising infecting host cells permissive for poxvirus infectivity with a recombinant poxvirus encoding a fusion protein comprising amino acids 20 to 243 of SEQ ID NO: 10 or amino acids 20 to 281 of SEQ ID NO: 11. In certain aspects the fusion protein can further comprise a signal peptide, e.g., amino acids 1 to 19 of SEQ ID NO: 10.

FZD-B5R (short)

(SEQ ID NO: 10)

MGWSCIILFLVATATGAYAFGDEEERRCDPIRISMCQNLG

YNVTKMPNLVGHELQTDAELQLTTFTPLIQYGCSSQLQF

FLCSVYVPMCTEKINIPIGPCGGMCLSVKRRCEPVLKEF

GFAWPESLNCSKFPPQNDHNHMCMEGPGDEEVPLPHKT

PIQPGEECHSVGTNSDQYIWVKRSLNCVLKCGYDAGLYS

RSAKEC_ATYHIIIVALTIMGVIFLISVIVLVCSCDKNNDQYKFHK_

_LLP_.

Single Underline—leader peptide (amino acids 1-19)
Bold—human FZD4 extracellular domain (amino acids 20-200)
Italics—B5R TM and cytoplasmic tail (amino acids 201-243)

FZD-B5R (long)

(SEQ ID NO: 11)

MGWSCIILFLVATATGAYAFGDEEERRCDPIRISMCQNLG

YNVTKMPNLVGHELQTDAELQLTTFTPLIQYGCSSQLQF

FLCSVYVPMCTEKINIPIGPCGGMCLSVKRRCEPVLKEF

GFAWPESLNCSKFPPQNDHNHMCMEGPGDEEVPLPHKT

PIQPGEECHSVGTNSDQYIWVKRSLNCVLKCGYDAGLYS

RSAKE*YVRTNEEFDPVDDGPDDETDLSKLSKDVVQYEQEIESL*

*EATYHIIIVALTIMGVIFLISVIVLVCSCDKNNDQYKFHKLLP.*

Single Underline—leader peptide (amino acids 1-19)
Bold—human FZD4 extracellular domain (amino acids 20-200)
Italics—B5R stalk, TM and cytoplasmic tail (amino acids 201-281)

The disclosure further provides a fusion protein comprising: amino acids 20 to 892 of SEQ ID NO: 2; SEQ ID NO: 3; SEQ ID NO: 4; amino acids 20 to 370 of SEQ ID NO: 6; amino acids 20 to 855 of SEQ ID NO: 7; amino acids 20 to 935 of SEQ ID NO: 8; amino acids 20 to 243 of SEQ ID NO: 10; or amino acids 20 to 281 of SEQ ID NO: 11, any combination thereof, any fragment thereof, or any variant thereof, where the fusion protein, when expressed by a recombinant poxvirus, appears on the surface of a poxvirus extracellular enveloped virion (EEV) in a native conformation.

A recombinant poxvirus EEV comprising any EEV fusion protein as provided herein is also provided.

Method of Selecting Antibodies

This disclosure further provides a method to select binding molecules, e.g., antibodies, antigen-binding antibody fragments, or antibody like binding molecules that bind to a multi-pass membrane protein interest. The method comprises attaching a recombinant EEV as provided herein to a solid support, where the recombinant EEV can display a multi-pass protein on its surface; providing a display library, e.g., an antibody display library, where the library comprises display packages displaying a plurality of antigen binding domains; contacting the display library with the EEV such that display packages displaying antigen binding domains that specifically binds to the IMP expressed on the EEV can bind thereto; removing unbound display packages; and recovering display packages that display an antigen binding domain specific for the IMP expressed on the EEV.

Any display library comprising a plurality of binding domains, e.g., antibodies, antibody like molecules or other binding molecules is suitable for this method. For example the display library can be a phage display library, a yeast display library or a library constructed in a vaccinia virus vector as described elsewhere herein.

In certain aspects, the recombinant EEV can be inactivated prior to attachment to the solid support. For example, the EEV can be inactivated by incubation with Psoralen (Trioxsalen, 4'-aminomethyl-, hydrochloride) in the presence of UV irradiation.

Any suitable solid support can be used. As used herein, a "solid support" is any support capable of binding an EEV, which can be in any of various forms, as is known in the art. Well-known supports include tissue culture plastic, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of this disclosure. The support material can have virtually any structural configuration as long as the coupled EEV is capable of binding to a displayed binding molecule such as an antibody. Thus, the support configuration can be spherical, as in a bead, or cylindrical, as in the inside surface of a test tube, or the external surface of a rod. Alternatively, the surface can be flat such as a sheet, test strip, etc. Typical supports include beads, e.g., magnetic polystyrene beads such as DYNABEADS® that can be pulled out of suspension by a magnet. The support configuration can include a tube, bead, microbead, well, plate, tissue culture plate, petri plate, microplate, microtiter plate, flask, stick, strip, vial, paddle, etc., etc. A solid support can be magnetic or non-magnetic. Those skilled in the art will know many other suitable carriers for binding EEV as provided herein, or will be able to readily ascertain the same. In certain aspects, EEV as provided herein can be attached to the solid support via reaction with, e.g., tosyl groups, epoxy groups, carboxylic acid groups, or amino groups attached to the surface. For example, EEV can be attached to the surface of tosyl-activated magnetic beads, e.g., MYONE™ tosylactivated beads. Alternatively, the EEV can be biotinylated and attached to a streptavidin solid surface, e.g., streptavidin coated magnetic beads.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freeman & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties. The following examples are offered by way of illustration and not by way of limitation.

EXAMPLES

Example 1: Fusion Protein Construction

Figure 1A:
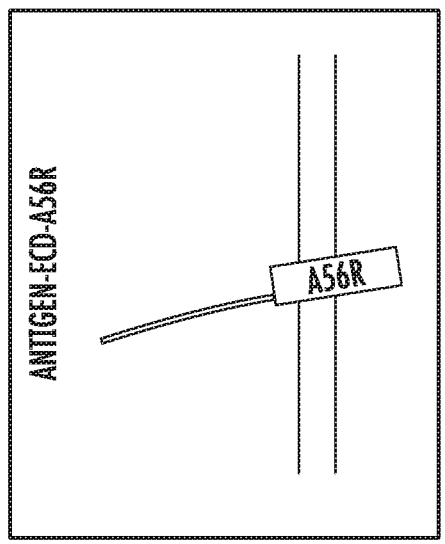

IMPs were incorporated into vaccinia virus EEVs using the EEV-specific proteins F13L, A56R, and B5R, by the following methods. Generally, the extracellular domains of HER2, CD100 (semaphorin 4D), and FZD4 were incorporated as fusions with the single-pass EEV-specific membrane proteins A56R and B5R as diagrammed in FIG. 1A. The mature FZD4-ECD-A56R fusion protein comprises amino acids 20 to 370 of SEQ ID NO: 6, the mature HER2-ECD-A56R fusion protein comprises amino acids 20 to 855 of SEQ ID NO: 7, and the mature CD100-ECD-A56R fusion protein comprises amino acids 20 to 935 SEQ ID NO: 8. FIG. 1B and FIG. 1C show diagrammatically how the multi-pass proteins such as GPCRs and CD20 can be incorporated into EEVs as multi-pass membrane proteins as a fusion with the EEV membrane-associated protein F13L.

Preparation of F13L Fusion Proteins (FZD4-F13L, CD20-F13L, and CXCR4-F13L)

cDNAs encoding the IMPs were cloned in-frame to the vaccinia virus F13L gene encoding the palmitoylated EEV membrane glycoprotein (SEQ ID NO: 1) into the pJEM1 plasmid previously described for the purpose of introduction into vaccinia virus. pJEM1 is a derivative of p7.5/tk described in U.S. Patent Appl. Publ. No. 2013/0288927, and when digested with NcoI or BssHII and BsiWI, contains flanking regions capable of homologous recombination with the vaccinia virus TK gene and the vaccinia virus H5 promoter.

The open reading frame of human membrane protein MS4A1 gene (CD20)(NM_021950.3) was cloned in frame with the vaccinia virus F13L using SOE (Splicing by Overlap Extension) PCR as per standard protocols whereby restriction endonuclease sites NcoI and BsiWI were added to the PCR product by encoding them into the 5' and 3'-most flanking primers respectively. This strategy avoids the introduction of a leader peptide. The final PCR product and pJEM1 were digested with NcoI and BsiWI and the two species were joined via ligation according to standard protocols. The circularized plasmid was then introduced into competent E. coli via chemical transformation and colonies were selected on ampicillin-containing agar plates.

```
MS4A1S
                                             (SEQ ID NO: 12)
tataCCATGgCAACACCCAGAAATTCAGTAAATG MS4A1AS
                                             (SEQ ID NO: 13)
GGTACCGATGCAAATGGCCACATAGGAGAGCTGTCATTTTCTATTGG F13S
                                             (SEQ ID NO: 14)
CCAATAGAAAATGACAGCTCTCCTATGTGGCCATTTGCATCGGTACC F13AS
                                             (SEQ ID NO: 15)
tataCGTACGTTAATGGTGATGGTGATGATGAATTTTTAACGATTTACTG
TG
```

The resulting CD20-F13L fusion protein encoded by the polynucleotide comprises the amino acid sequence SEQ ID NO: 4.

The open reading frame of human membrane protein FZD4 (NM_012193.3) was cloned in frame with the vaccinia virus F13L using SOE (Splicing by Overlap Extension) PCR as per standard protocols whereby restriction endonuclease sites BssHII and BsiWI were added to the PCR product by encoding them into the 5' and 3'-most flanking primers, respectively. This strategy provides for the use of the leader peptide contained within pJEM1. The final PCR product and pJEM1 were digested with BssHII and BsiWI and the two species were joined via ligation according to the standard protocols. The circularized plasmid was then introduced into competent E. coli via chemical transformation and colonies were selected on ampicillin-containing agar plates. PCR primers were specific for FZD4 and F13L and conform to the same general strategy as described for MS4A1. The resulting mature FZD4-F13L fusion protein encoded by the polynucleotide comprises amino acids 20-892 of SEQ ID NO: 2.

The open reading frame of human membrane protein CXCR4 (NM_001008540.1) was cloned in frame with the vaccinia virus F13L using SOE (Splicing by Overlap Extension) PCR as per standard protocols whereby restriction endonuclease sites NcoI and BsiWI were added to the PCR product by encoding them into the 5' and 3'-most flanking primers respectively. This strategy avoids the introduction of a leader peptide. The final PCR product and pJEM1 were digested with NcoI and BsiWI and the two species were joined via ligation according to the standard protocol. The circularized plasmid was then introduced into competent E. coli via chemical transformation and colonies were selected on ampicillin-containing agar plates. PCR primers were specific for CXCR4 and F13L and conform to the same general strategy as described for MS4A1. The resulting CXCR4-F13L fusion protein encoded by the polynucleotide comprises the amino acid sequence SEQ ID NO: 3.

The plasmids produced as described above, as well as similar plasmids encoding non-fused ("untagged") versions of CD20, FZD4, CXCR4, CD100, and HER2, were linearized and introduced into vaccinia virus via tri-molecular recombination.

Example 2: Expression of CD20-F13L Fusion Protein on EEV

BHK cells were infected with either IMV encoding the CD20-F13L fusion protein (SEQ ID NO: 4) or Control Western Reserve (WR) virus at a multiplicity of infection (MOI) of 1 virus per cell for two days after which the supernatant containing EEV was harvested and debris removed by low speed centrifugation. Protein G DYNABEADS® (110 μL) were pulled down with a magnet and 1 mL of PBS+20 μg of purified anti-CD20 antibody was added to the beads. The solution was incubated at room temperature with gentle rotation for 30-60 minutes to allow the antibody to couple to the Protein G beads. Ten μg of purified mIgG1 isotype control was added to the solution to ensure complete blocking, and the solution was incubated at room temperature with gentle rotation for 10-30 additional minutes. Beads were pulled down with the magnet, washed once with 1 mL of PBS and resuspended in 110 μL of PBS.

Fifty μL of Anti-CD20-Pro G DYNABEADS® was added to 1 mL of CD20-F13L or WR EEV supernatant and was incubated at room temperature with gentle rotation for 1 hour. Beads were pelleted using the magnet and unbound supernatant removed. The beads were then washed five times with 1 mL of Dulbecco's Modified Eagle Medium (DMEM) media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. Results are shown on Table 2.

TABLE 2

| CD20-F13L EEV Binding | |
| --- | --- |
| EEV Supernatant | % Bound |
| Western Reserve | 10.8% |
| CD20-F13L | 50.5% |

The % EEV bound to the anti-CD20 coated beads was significantly higher for CD20-F13L EEV fusion protein than it is for the Western Reserve indicating that CD20 is being expressed on the EEV membrane surface.

Example 3: Fusion of CD20 to F13L is More Efficiently Expressed on the EEV Membrane BHK cells were infected with either IMV encoding the CD20-F13L fusion protein (SEQ ID NO: 4), CD20-A56R fusion protein (SEQ ID NO: 16 CD20 untagged (unfused) or control HER2-A56R Extracellular Domain (ECD) (SEQ ID NO: 7) virus at an MOI=1 for two days after which the supernatant containing EEV was harvested and debris removed by low speed centrifugation. Streptavidin DYNABEADS® (200 μL) were pulled down with a magnet and 0.2 mL of PBS+20 μg of purified Biotinylated anti-CD20 antibody or Biotinylated anti-HER2 was added to the beads. The solution was incubated at room temperature with gentle rotation for 30 minutes to allow the antibody to couple to the Streptavidin beads. Beads were pulled down with the magnet, washed once with 1 mL of PBS and resuspended in 200 μL of PBS.

CD20-A56R:

(SEQ ID NO: 16)

MGWSCIILFLVATATGAHT*ELIVNTDSESTIDIILSGSTHSPETS*

*SKKPDYIDNSNCSSVFEIATPEPITDNVEDHTDTVTYTSDSINTVS*

*ASSGESTTDETPEPITDKEDHTVTDTVSYTTVSTSSGIVTTKSTTD*

*DADLYDTYNDNDTVPPTTVGGSTTSISNYKTKDFVEIFGITALIIL*

*SAVAIFCITYYIYNKRSRKYKTENKV*MTTPRNSVNGTFPAEPM

KGPIAMQSGPKPLFRRMSSLVGPTQSFFMRESKTLGAVQ

IMNGLFHIALGGLLMIPAGIYAPICVTVWYPLWGGIMYII

SGSLLAATEKNSRKCLVKGKMIMNSLSLFAAISGMILSIM

DILNIKISHFLKMESLNFIRAHTPYINIYNCEPANPSEKNSP

STQYCYSIQSLFLGILSVMLIFAFFQELVIAGIVENEWKRT

CSRPKSNIVLLSAEEKKEQTIEIKEEVVGLTETSSQPKNE

EDIEIIPIQEEEEEETETNFPEPPQDQESSPIENDSSP

Single Underline—Signal sequence (amino acids 1-19)
Italics—Truncated A56R (amino acids 20-190)
Bold—CD20 Sequence (amino acids 191-506)

Figure 2:
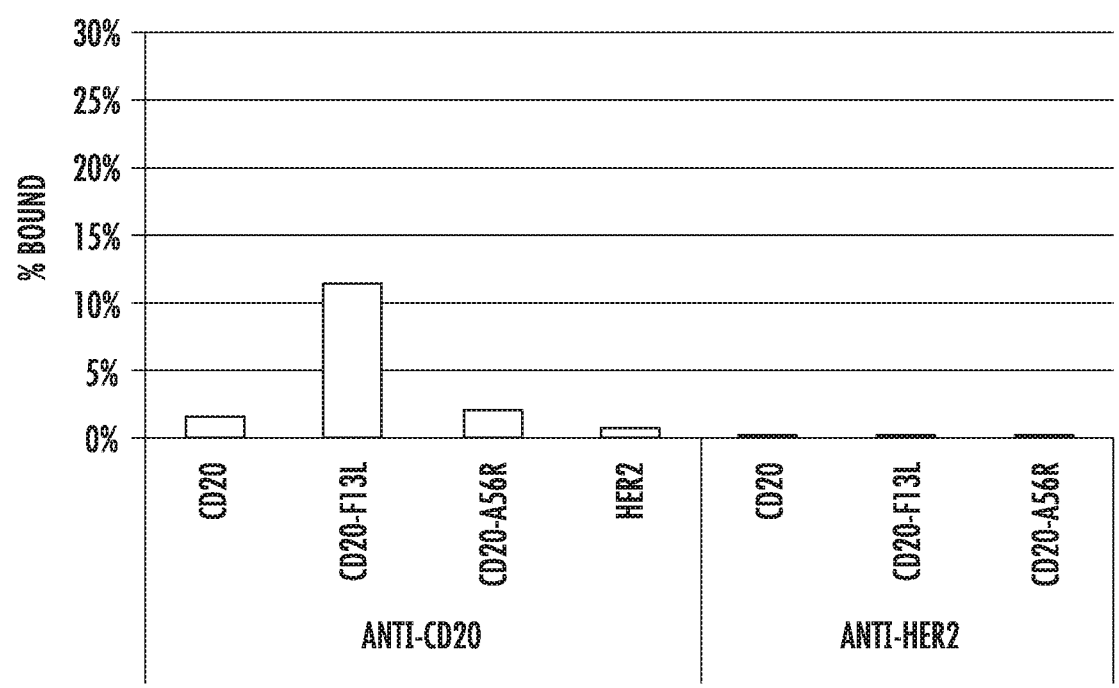

Fifty μL of prepared streptavidin beads were added to 1 mL of each EEV supernatant and allowed to rotate at room temperature for 45 minutes. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. Results are shown in FIG. 2.

The % EEV bound to the anti-CD20 coated beads for CD20-F13L was greater than the % EEV bound for untagged (unfused) or A56R-fused CD20 indicating higher expression of CD20-F13L on the EEV membrane. The lack of binding to the anti-HER2 coated beads confirmed specificity of the assay.

Figure 3A:
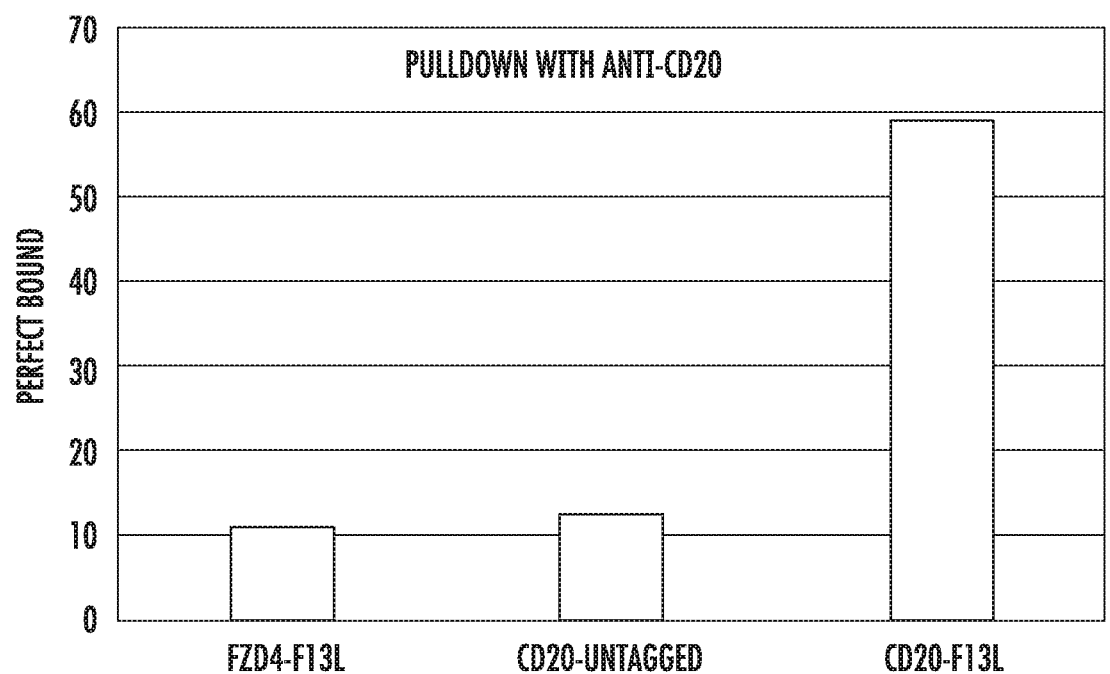
Figure 3B:
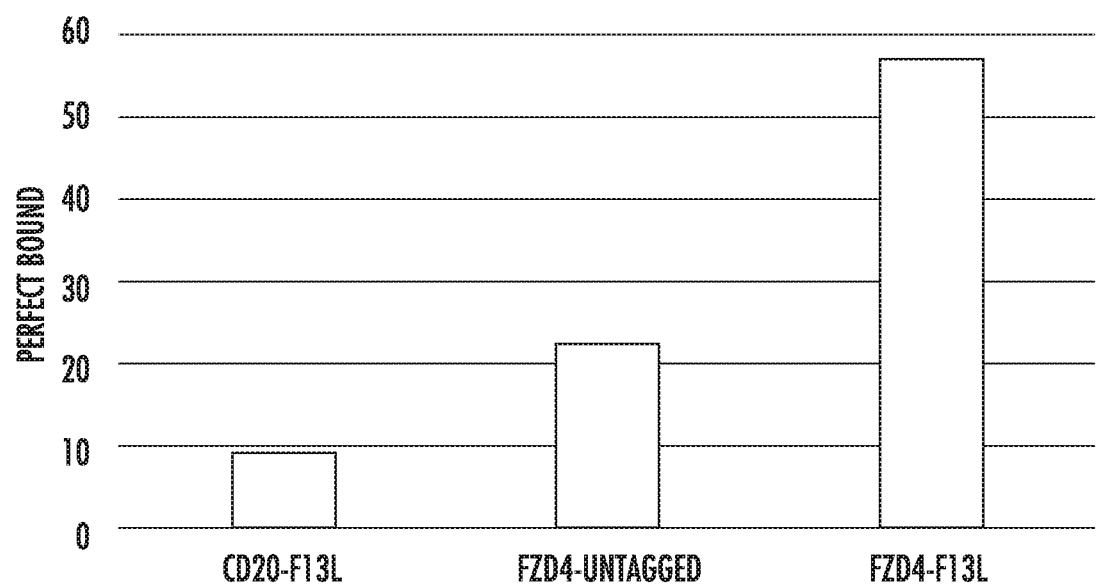

The experiment above was repeated using CD20-F13L fusion protein (SEQ ID NO: 4), CD20 untagged (unfused), FZD-F13L fusion protein (SEQ ID NO: 2), and FZD untagged (unfused). Virus was pulled down using anti-CD20 or anti-FZD coated beads as described above. The data in FIG. 3A (anti-CD20-coated beads) and FIG. 3B (anti-FZD-coated beads) shows that F13L fusion proteins were specifically pulled down by their respective antibodies, and were more efficiently incorporated into vaccinia virus than untagged (unfused) proteins.

Example 4: Vaccinia Virus can be Engineered to Express Various Antigen-EEV Constructs BHK cells were infected at an MOI=1 with virus expressing the following antigen constructs: CD20-F13L (SEQ ID NO: 4), CXCR4-F13L (SEQ ID NO: 3), HER2-ECD-A56R (SEQ ID NO: 7), and CD100-ECD-A56R (SEQ ID NO: 8). After two days, the supernatant containing EEV was harvested and debris removed by low speed centrifugation. Streptavidin DYNABEADS® were pulled down with a magnet and for each sample, 50 of beads were resuspended in 0.1 mL of PBS+5 µg of purified Biotinylated anti-CD20 antibody, Biotinylated anti-CXCR4 (12G5), Biotinylated anti-CD100 (2503), or Biotinylated anti-HER2. The solutions were incubated at room temperature with gentle rotation for 30 minutes to allow the antibody to couple to the Streptavidin beads. Beads were pulled down with the magnet, washed once with 1 mL of PBS and resuspended in 100 µL of PBS per sample.

Figure 4:
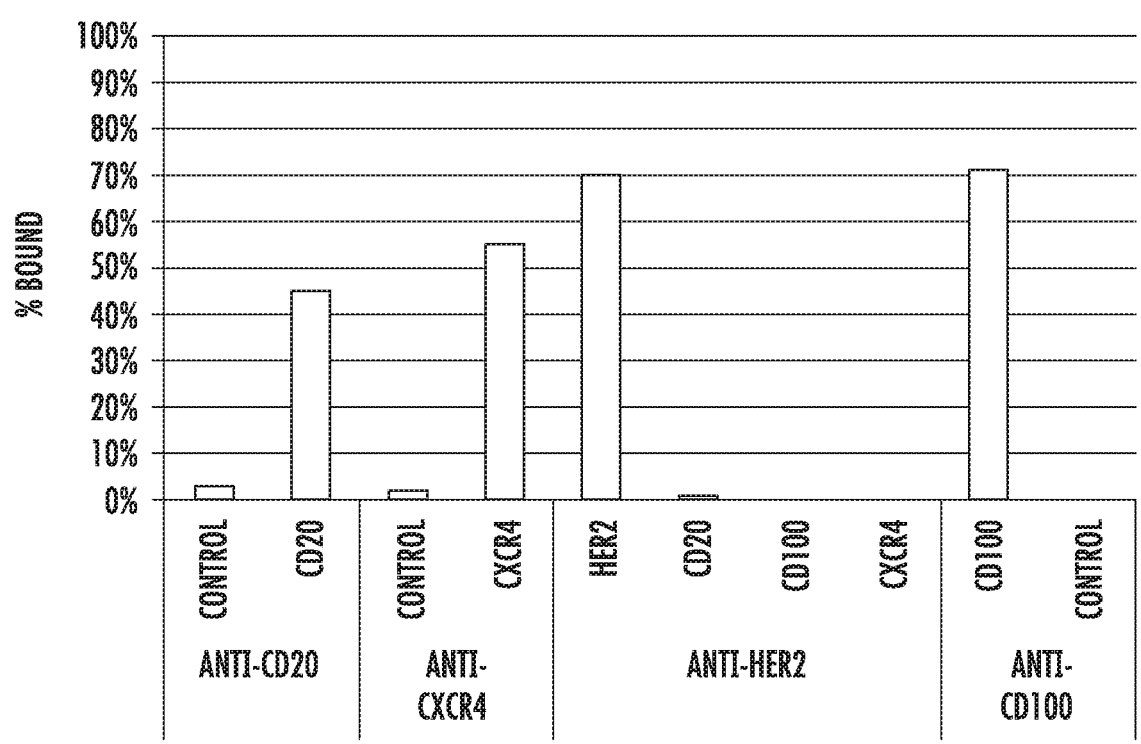
Figure 7:
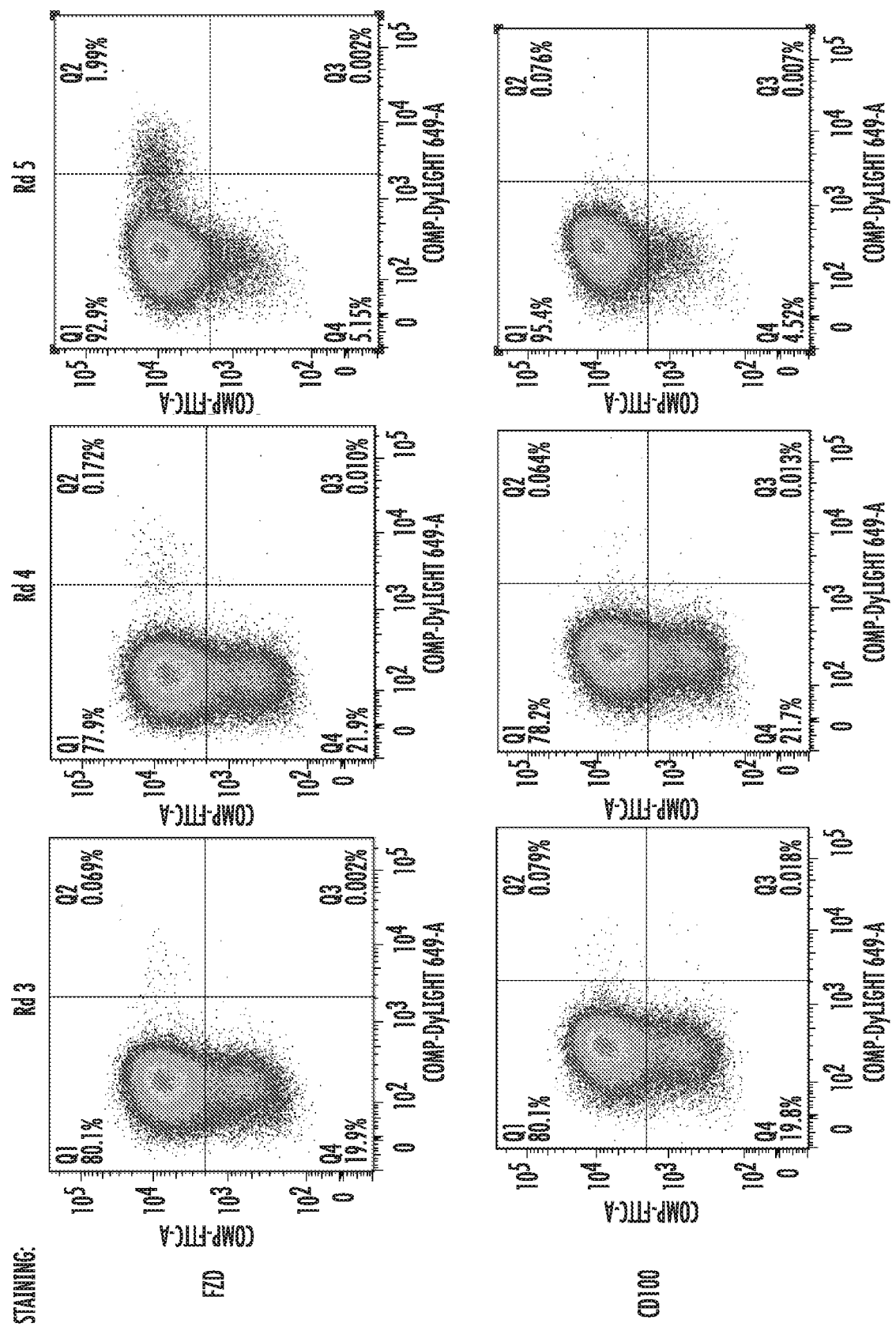
Figure 8:
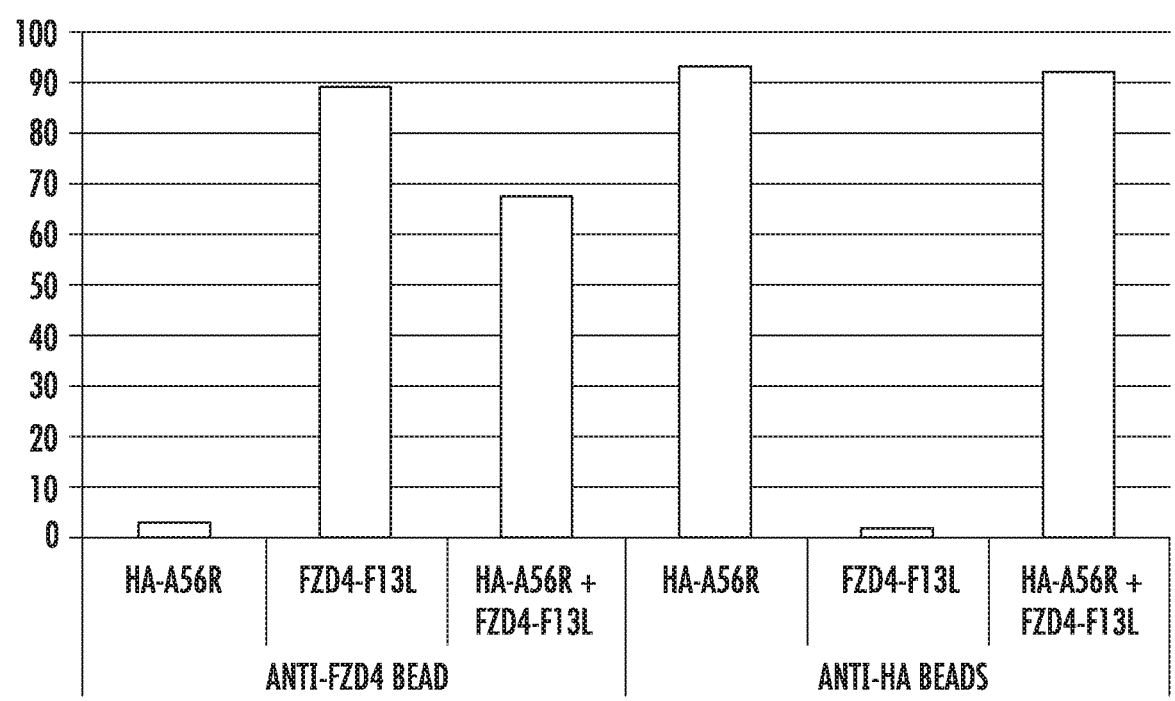

One hundred µL of prepared streptavidin beads were added to 1 mL of each EEV supernatant and allowed to rotate at room temperature for 45 minutes. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. Results are shown in FIG. 4.

All of the antigen-EEV bound specifically to their corresponding antibody-coupled beads indicating efficient expression of the antigen on the EEV membrane.

Example 5: Antigen-EEV can be Directly Coupled to Magnetic Beads for Antibody Selection BHK cells ($2 \times 10^8$ cells) were infected at an MOI=1 with virus expressing HER2-ECD-A56R (SEQ ID NO: 7), FZD-F13L (SEQ ID NO: 2), CXCR4-F13L (SEQ ID NO: 3) or CD100 (semaphorin 4D)-ECD-A56R (SEQ ID NO: 8) in one cellSTACK cell culture chamber each (Corning). After two days, the supernatant containing EEV was harvested and debris removed by low speed centrifugation. The clarified supernatant was then spun at 13,000 rpm (28,000×g) for 1 hour to pellet the antigen-EEV. The supernatant was aspirated and the pellet resuspended in 1.5 mL of 1×PBS. The various viruses were transferred to fresh tubes and Psoralen (Trioxsalen, 4'-aminomethyl-, hydrochloride; Sigma) was added to 20 µg/ml final concentration. The EEV and Psoralen were incubated at room temperature for 10 minutes before being irradiated in the STRATALINKER® UV Crosslinker (Stratagene) for 99,999 microjoules. The Psoralen/UV procedure ensures that the antigen-EEV is inactivated and therefore unable to form plaques or multiply in any downstream testing.

Tosylactivated MyOne DYNABEADS® (100 µL) were pulled down with a magnet and washed with 1 mL of PBS. The beads were pulled down with the magnet, the PBS removed and 1 mL of each Psoralen/UV inactivated antigen-EEV was added to a separate aliquot of beads. The beads and antigen-EEV were allowed to rotate at 37° C. for 16-20 hours. The beads were pelleted and the supernatant was removed. The beads were blocked with 1 mL of 1×PBS, 10% FBS and 0.5% BSA at 37° C. for 1 hour. The beads were pelleted and washed with 1 mL 1×PBS before being resuspended in 200 µL of 1×PBS.

One hundred microliters of antigen-EEV-coupled beads was added to 1 mL of each respective antibody-EEV supernatant expressing anti-FZD4, anti-CXCR4, anti-CD100, or anti-HER2, as well as to control antibody-EEV. Antibody EEV were produced by infecting BHK cells at an MOI=1 each for 2 days with vaccinia virus encoding both the heavy and light chains of the respective antibodies, and harvesting the supernatants followed by a low speed spin to remove any cells. The virus coupled beads and antibody EEV were allowed to rotate at room temperature for 2 hours. Beads were pelleted using the magnet and unbound supernatants removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. A diagram of the method is shown in FIG. 5, and results are shown in FIG. 6A (HER2), FIG. 6B (FZD4), FIG. 6C (CXCR4), and FIG. 6D (CD100 ("Sema")).

Antibody-EEV expressing Anti-HER2 was specifically pulled down by beads coupled with HER2-ECD-A56R antigen EEV, Antibody-EEV expressing Anti-FZD was specifically pulled down by beads coupled with FZD-F13L antigen EEV, Antibody-EEV expressing Anti-CXCR4 was specifically pulled down by beads coupled with CXCR4-F13L antigen EEV, and Antibody-EEV expressing Anti-SEMA was specifically pulled down by beads coupled with Sema-ECD-A56R antigen EEV.

Example 6: Antibody Library Screening

BHK cells were infected at an MOI=1 each with an antibody library (H-IgG-A56R) and L48 (derivative of germline VK1-39) in four cellSTACK cell culture chamber (Corning) ($2 \times 10^8$ cells per stacker). The antibody library contained a diverse population of heavy chain variable domains in full length IgG format, fused in frame to A56R (see US Patent Appl. Publication No. 2013-0288927, which is incorporated herein by reference in its entirety). The diversity of this library was approximately 400 million independent clones. After two days, the supernatant containing EEV was harvested and debris removed by low speed centrifugation. The clarified supernatant was then spun at 13,000 rpm (28,000×g) for 1 hour to pellet the antibody-EEV. The antibody-EEV was resuspended in 1 ml EMEM with 10% FBS and stored at 4 degrees until ready for use. In order to make the antigen virus for panning, BHK cells ($2 \times 10^8$ cells) were infected at an MOI=1.5 with virus expressing FZD4-ECD-A56R (SEQ ID NO: 6) in two cellSTACK cell culture chamber (Corning). After two days, the supernatant containing EEV was harvested and debris removed by low speed centrifugation. The clarified supernatant was then spun at 13,000 rpm (28,000×g) for 1 hour to pellet the antigen-EEV. The supernatant was aspirated and the pellet resuspended in 1.0 mL of 1×PBS. The one mL of the FZD4-ECD-A56R EEV was transferred to a fresh tube and Psoralen (Trioxsalen, 4'-aminomethyl-, hydrochloride; Sigma) was added to 40 µg/ml final concentration. The EEV and Psoralen were incubated at room temperature for 10 minutes before being irradiated in the STRATALINKER® UV Crosslinker (Stratagene) for 99,999 microjoules. The Psoralen/UV procedure ensures that the antigen-EEV is inactivated and therefore unable to form plaques or multiply in any downstream testing.

Tosylactivated MyOne DYNABEADS® (150 μL) were pulled down with a magnet and washed with 1 mL of PBS, two times. The beads were pulled down with the magnet, the PBS removed and the 1 mL of Psoralen/UV inactivated FZD4-ECD-A56R was added to the beads. The beads and antigen-EEV were allowed to rotate at 37° C. for 18-20 hours. The beads were pelleted and the supernatant was removed. The beads were blocked with 1 mL of 1×PBS, 10% FBS and 0.5% BSA at 37° C. for 2 hours. The beads were pelleted and washed with 1 mL 1×PBS before being resuspended in 150 μL of 1×PBS.

Fifty microliters of FZD4-ECD-A56R-coupled beads were added to 1 mL of the antibody-EEV library. The FZD4-ECD-A56R coupled beads and antibody EEV were allowed to rotate at room temperature for 2 hours. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. The remaining bound virus (990 μl) was divided among 5 T175 flasks containing confluent BSC1 cells and allowed to amplify in DMEM2.5% containing 1 mg/ml G418 for 3 days. The cells were then harvested, and the virus released by three cycles of freeze/thaw, and the virus titered.

For the second round of selection (Rd2), the amplified Heavy chains from round 1 were co-infected along with fresh L48 into one cellSTACK of BHK. Antibody EEV was harvested as described above. For each round of panning, fresh FZD-ECD-A56R antigen virus was produced, concentrated, inactivated and coupled to beads as described above. Fifty microliters of FZD4-ECD-A56R coupled beads was added to 1 mL antibody-EEV Rd2. The FZD4-ECD-A56R coupled beads and antibody EEV were allowed to rotate at room temperature for 2 hours. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. The remaining bound virus (990 ul) was divided among 5 T175 flasks containing confluent BSC1 cells and allowed to amplify in DMEM2.5% containing 1 mg/ml G418 for 3 days. The cells were then harvested, and the virus released by three cycles of freeze/thaw, and the virus tittered.

Three additional cycles of panning (Rd3, Rd4, and Rd5) were performed as described above.

Rounds 3, 4 and 5 were tested for enrichment by infected A431 cells in 6 well plate at moi=1 with each amplified VH round and L48. After an overnight infection the cells were harvested and split in half. One half was stained with 10 μg/ml FZD-His, followed by anti-His-Dyelight650 and anti-Fab-FITC. The other half was stained with 10 μg/ml CD100-His (negative control), followed by anti-His-Dyelight650 and anti-Fab-FITC. The data shown in FIG. 7 shows increasing enrichment per round of selection. Antibodies from round 5 were sub-cloned into a mammalian expression vector to be expressed as full length soluble IgG and transfected (along with L48 in a mammalian expression vector). The resulting antibodies present in the supernatant were tested by flow cytometry for binding to FZD4 transfected CHO cells and the absence of binding to CXCR4 transfected CHO cells. A number of antibodies that bound specifically to FZD were identified.

Example 7: Dual Tag/Antigen EEV can be Coupled to Magnetic Beads

BHK cells were infected at two virions per cell where one virion was Hemagglutinin tag (HA)-A56R (SEQ ID NO: 17) and the second was FZD4-F13L (SEQ ID NO: 2) in order to yield EEV expressing both the HA tag and FZD4 antigen on its surface or infected at one virion per cell with each individual virus. After two days, the supernatant containing EEV was harvested and debris removed by low speed centrifugation. Protein G magnetic beads (150 μL) were pulled down with a magnet and 1 mL of PBS+30 μg of purified anti-FZD4 antibody (C6073) was added to the beads. The solution was incubated at room temperature with gentle rotation for 25 minutes to allow the antibody to couple to the Protein G beads. Beads were pulled down with the magnet, washed once with 1 mL of PBS and resuspended in 300 μL of DMEM+10% FBS. Anti-HA-tag magnetic beads (ThermoFisher, 150 μl) pulled down with a magnet and washed once with 1 mL of PBS before resuspending in 150 μl of PBS.

HA-A56R (SEQ ID NO: 17)

<u>*MGWSCIILFLVATATGAHS*</u>YPYDVPDYA*TSTTNDTDKVDYEEYS*

*TELIVNTDSESTIDIILSGSTHSPETSSKKPDYIDNSNCSSVFEIATP*

*EPITDNVEDHTDTVTYTSDSINTVSASSGESTTDETPEPITDKED*

HTVTDTVSYTTVSTSSGIVTTKSTTDDADLYDTYNDNDTVPPTTV

*GGSTTSISNYKTKDFVEIFGITALIILSAVAIFCITYYIYNKRSRKYK*

*TENKV*

Single Underline—Signal sequence (amino acids 1-19)
Bold—HA Tag (amino acids 20-29)
Italics—Truncated A56R (amino acids 30-235)

Fifty μL of prepared anti-HA-tag beads or 100 μl of prepared anti-FZD4 Protein G were added to 1 mL of each EEV supernatant and allowed to rotate at room temperature for 60 minutes. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. Results are shown in FIG. 8. EEV expressing both fusion proteins were pulled down by either antibody.

Example 8: Dual Tag/Antigen EEV can be Coupled to Magnetic Beads and Used to Capture mAb EEV BHK cells (2×10$^8$ cells) were infected at two virions per cell where one virion was HA-A56R (SEQ ID NO: 17) and the second was CXCR4-F13L (SEQ ID NO: 3) in order to yield EEV expressing both the HA tag and CXCR4 antigen on its surface. After two days, the supernatant containing EEV was harvested and debris removed by low speed centrifugation. The clarified supernatant was then spun at 13,000 rpm (28,000×g) for 1 hour to pellet the tag/antigen-EEV. The supernatant was aspirated and the pellet resuspended in 1 mL of 1×PBS. Psoralen (Trioxsalen, 4'-aminomethyl-, hydrochloride; Sigma) was added to 40 ug/ml final concentration. The EEV and Psoralen were incubated at room temperature for 10 minutes before being irradiated in the Stratalinker UV Crosslinker (Stratagene) for 99,999 microjoules twice. The Psoralen/UV procedure ensures that the antigen-EEV is inactivated and therefore unable to form plaques or multiply in any downstream testing.

Anti-CXCR4 EEV and anti-HER2 mAb EEV were produced by infecting BHK cells at two virions per cell where one virion was specific heavy chain and the second was specific light chain. After two days, supernatants containing the anti-CXCR4 EEV and the anti-HER2 EEV were harvested and debris removed by low speed centrifugation.

Three hundred microliters of anti-HA magnetic beads were washed with 1 mL of PBS and then resuspended in one milliliter of the Psoralen/UV inactivated HA/CXCR4 EEV. The beads and EEV were incubated at room temperature with gentle rotation for 90 minutes to allow the EEV to couple with the anti-HA beads. Beads were pulled down with the magnet, washed once with 1 mL of PBS and resuspended in 300 µL of PBS.

Figure 9:
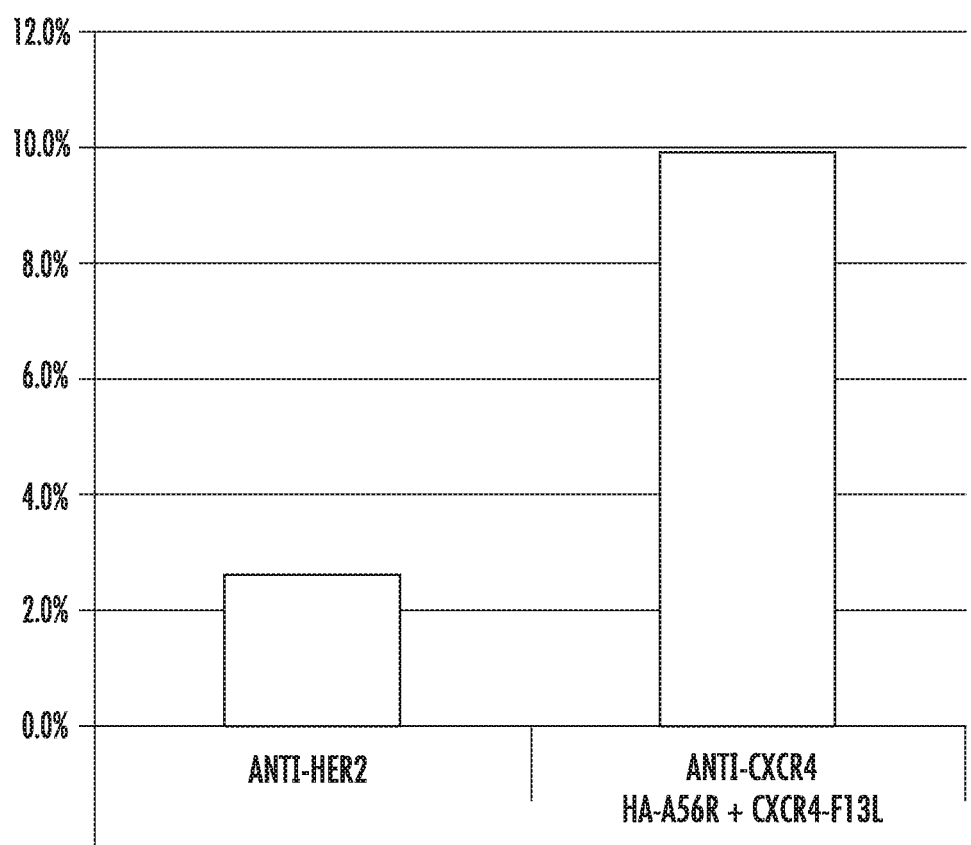

One hundred µL of HA/CXCR4 EEV coupled to the anti-HA beads was added to 1 mL of each mAb EEV supernatant and incubated at room temperature with gentle rotation for 1-1.5 hours. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. Results are shown in FIG. 9. Anti-CXCR4 EEV were specifically captured by the beads coated with EEV co-expressing HA-A45R and CXCR4-F13L.

Example 9: Antigen-EEV can be Biotinylated for Coupling to Magnetic Beads

BHK cells were infected at an MOI=1 with virus expressing FZD4-F13L, FZD4-ECD-A56R or CD20-F13L. After two days, the supernatant containing EEV was harvested and debris removed by low speed centrifugation. The clarified supernatant was then spun at 13,000 rpm for 1 hour to pellet the antigen-EEV. The supernatant was aspirated and the pellet resuspended in 1-2 mL of 1×PBS. To biotinylate the EEV, 2.5 µL of Biotin-XX SSE stock solution in 1×PBS (FLUOREPORTER® Cell Surface Biotinylation Kit, Molecular Probes) was added to the 1 mL of each EEV in PBS and incubated on ice for 30 minutes. Fifty µL of 1M Tris, pH 8 was added to quench each reaction.

Figure 10:
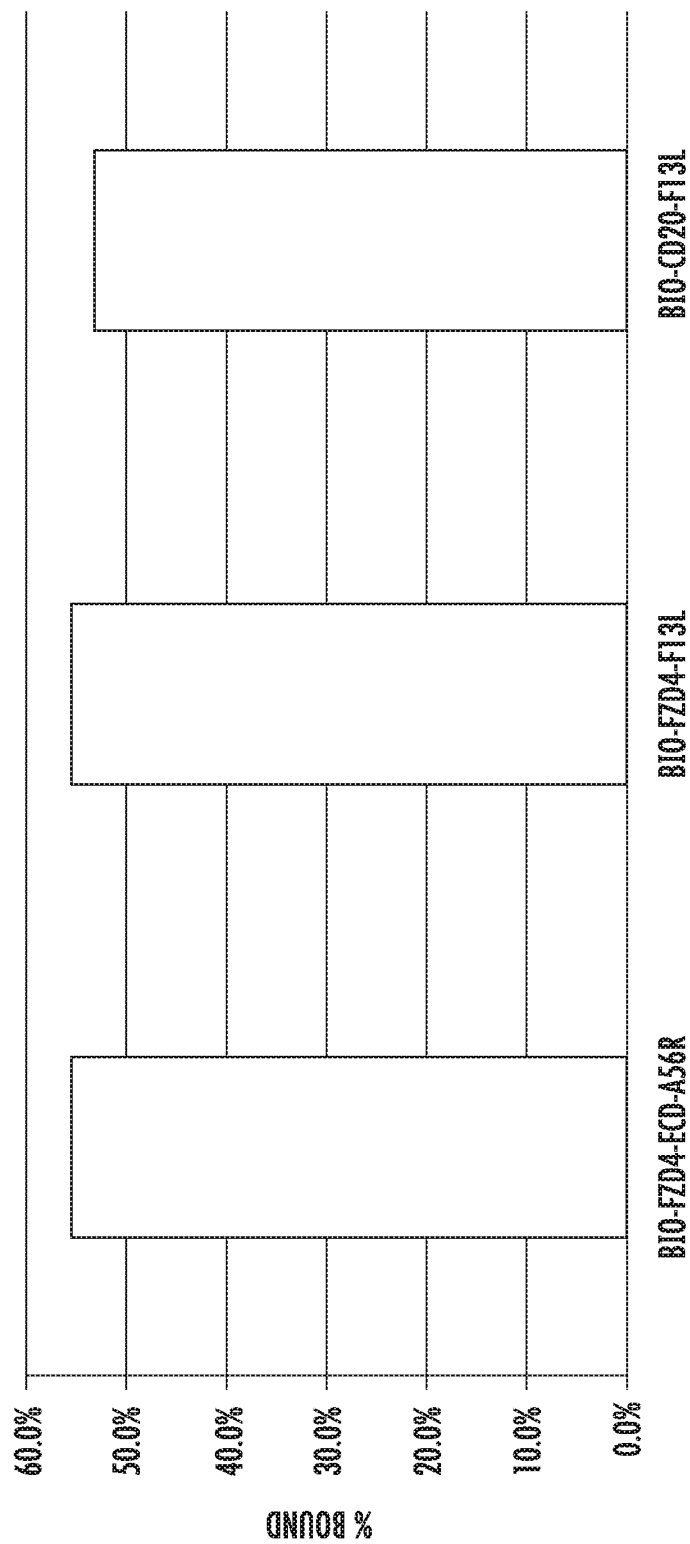

To couple the Biotin-EEV to beads, 150 µL of Streptavidin DYNABEADS® were pelleted and washed once with 1 mL of 1×PBS. The beads were resuspended in 150 µL and 50 µL was added to 1 mL of Eagle's Minimum Essential Medium (EMEM) media containing 10% FBS and 1 mM HEPES (10% EMEM). Fifty µL of Biotin-EEV was added to the beads and media and allowed to rotate at room temperature for 1 hour. Beads were pelleted using the magnet and unbound supernatant removed. The beads were then washed five times with 1 mL of DMEM media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on BSC-1 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. Results are shown in FIG. 10.

Antigen-EEV was able to be biotinylated and coupled to magnetic Streptavidin beads.

---

What is claimed is:

1. An IMP-EEV fusion protein, which comprises
    (a) an integral membrane protein (IMP) or fragment thereof, which comprises at least one extra-membrane region, at least one transmembrane domain, and at least one intra-membrane region; and
    (b) a vaccinia virus extracellular enveloped virion (EEV) protein or functional fragment thereof.

2. The IMP-EEV fusion protein of claim 1, comprising:
    (a) amino acids 20 to 892 of SEQ ID NO: 2;
    (b) SEQ ID NO: 3;
    (c) SEQ ID NO: 4;
    (d) amino acids 20 to 370 of SEQ ID NO: 6;
    (e) amino acids 20 to 855 of SEQ ID NO: 7;
    (f) amino acids 20 to 935 of SEQ ID NO: 8;
    (g) amino acids 20 to 243 of SEQ ID NO: 10; or
    (h) amino acids 20 to 281 of SEQ ID NO: 11.

3. A recombinant poxvirus EEV, comprising the IMP-EEV fusion protein of claim 2.

4. A recombinant poxvirus EEV, comprising the IMP-EEV fusion protein of claim 1, wherein the IMP or fragment thereof is heterologous to the EEV protein fused thereto, wherein the IMP-EEV fusion protein is situated in the outer envelope membrane and the IMP or fragment thereof is displayed on the surface of the outer membrane in its native conformation.

5. The recombinant poxvirus EEV of claim 4, wherein the poxvirus EEV is a vaccinia virus EEV.

6. A method of selecting antibodies that bind to a multi-pass membrane protein, which comprises:
    (a) attaching a vaccinia virus that expresses the IMP-EEV fusion protein of claim 1, wherein the IMP or fragment thereof is expressed on the surface of its outer membrane protein, to a solid support;
    (b) providing an antibody display library, wherein the library comprises display packages displaying a plurality of antigen binding domains;
    (c) contacting the display library with the vaccinia virus such that display packages displaying antigen binding domains that specifically binds to the IMP can bind thereto;
    (d) removing unbound display packages; and
    (e) recovering display packages having antigen binding domains bound to the IMP or fragment thereof.

7. The method of claim 6, wherein the vaccinia virus is attached to the solid surface via reaction with tosyl groups on the solid surface.

8. The method of claim 7, wherein the solid surface is tosyl-activated magnetic beads.

9. The method of claim 6, wherein the vaccinia virus is biotinylated and attached to a streptavidin coated solid surface.

10. The method of claim 9, wherein the solid surface is streptavidin-coated magnetic beads.

11. The IMP-EEV fusion protein of claim 1, wherein the IMP or fragment thereof is fused at its C-terminus to the EEV protein.

12. The IMP-EEV fusion protein of claim 1, wherein the IMP or fragment thereof is fused at its N-terminus to the EEV protein.

\* \* \* \* \*

SEQUENCE LISTING

```
<160> NUMBER OF SEQ ID NOS: 17

<210> SEQ ID NO 1
<211> LENGTH: 372
<212> TYPE: PRT
<213> ORGANISM: Artificial Sequence
<220> FEATURE:
<223> OTHER INFORMATION: F13L

<400> SEQUENCE: 1

Met Trp Pro Phe Ala Ser Val Pro Ala Gly Ala Lys Cys Arg Leu Val
1               5                   10                  15

Glu Thr Leu Pro Glu Asn Met Asp Phe Arg Ser Asp His Leu Thr Thr
            20                  25                  30

Phe Glu Cys Phe Asn Glu Ile Ile Thr Leu Ala Lys Lys Tyr Ile Tyr
```

```
            35                  40                  45
Ile Ala Ser Phe Cys Cys Asn Pro Leu Ser Thr Thr Arg Gly Ala Leu
 50                  55                  60

Ile Phe Asp Lys Leu Lys Glu Ala Ser Glu Lys Gly Ile Lys Ile Ile
 65                  70                  75                  80

Val Leu Leu Asp Glu Arg Gly Lys Arg Asn Leu Gly Glu Leu Gln Ser
                 85                  90                  95

His Cys Pro Asp Ile Asn Phe Ile Thr Val Asn Ile Asp Lys Lys Asn
                100                 105                 110

Asn Val Gly Leu Leu Gly Cys Phe Trp Val Ser Asp Glu Arg
            115                 120                 125

Cys Tyr Val Gly Asn Ala Ser Phe Thr Gly Gly Ser Ile His Thr Ile
            130                 135                 140

Lys Thr Leu Gly Val Tyr Ser Asp Tyr Pro Pro Leu Ala Thr Asp Leu
145                 150                 155                 160

Arg Arg Arg Phe Asp Thr Phe Lys Ala Phe Asn Ser Ala Lys Asn Ser
                165                 170                 175

Trp Leu Asn Leu Cys Ser Ala Ala Cys Cys Leu Pro Val Ser Thr Ala
            180                 185                 190

Tyr His Ile Lys Asn Pro Ile Gly Gly Val Phe Phe Thr Asp Ser Pro
            195                 200                 205

Glu His Leu Leu Gly Tyr Ser Arg Asp Leu Asp Thr Asp Val Val Ile
            210                 215                 220

Asp Lys Leu Lys Ser Ala Lys Thr Ser Ile Asp Ile Glu His Leu Ala
225                 230                 235                 240

Ile Val Pro Thr Thr Arg Val Asp Gly Asn Ser Tyr Tyr Trp Pro Asp
                245                 250                 255

Ile Tyr Asn Ser Ile Ile Glu Ala Ala Ile Asn Arg Gly Val Lys Ile
            260                 265                 270

Arg Leu Leu Val Gly Asn Trp Asp Lys Asn Asp Val Tyr Ser Met Ala
            275                 280                 285

Thr Ala Arg Ser Leu Asp Ala Leu Cys Val Gln Asn Asp Leu Ser Val
290                 295                 300

Lys Val Phe Thr Ile Gln Asn Asn Thr Lys Leu Leu Ile Val Asp Asp
305                 310                 315                 320

Glu Tyr Val His Ile Thr Ser Ala Asn Phe Asp Gly Thr His Tyr Gln
                325                 330                 335

Asn His Gly Phe Val Ser Phe Asn Ser Ile Asp Lys Gln Leu Val Ser
            340                 345                 350

Glu Ala Lys Lys Ile Phe Glu Arg Asp Trp Val Ser Ser His Ser Lys
            355                 360                 365

Ser Leu Lys Ile
        370

<210> SEQ ID NO 2
<211> LENGTH: 892
<212> TYPE: PRT
<213> ORGANISM: Artificial Sequence
<220> FEATURE:
<223> OTHER INFORMATION: FZD (FL) - F13L Fusion Protein

<400> SEQUENCE: 2

Met Gly Trp Ser Cys Ile Ile Leu Phe Leu Val Ala Thr Ala Thr Gly
 1               5                  10                  15

Ala His Ser Phe Gly Asp Glu Glu Glu Arg Arg Cys Asp Pro Ile Arg
```

```
            20                  25                  30
Ile Ser Met Cys Gln Asn Leu Gly Tyr Asn Val Thr Lys Met Pro Asn
                35                  40                  45
Leu Val Gly His Glu Leu Gln Thr Asp Ala Glu Leu Gln Leu Thr Thr
            50                  55                  60
Phe Thr Pro Leu Ile Gln Tyr Gly Cys Ser Ser Gln Leu Gln Phe Phe
65                  70                  75                  80
Leu Cys Ser Val Tyr Val Pro Met Cys Thr Glu Lys Ile Asn Ile Pro
                85                  90                  95
Ile Gly Pro Cys Gly Gly Met Cys Leu Ser Val Lys Arg Arg Cys Glu
            100                 105                 110
Pro Val Leu Lys Glu Phe Gly Phe Ala Trp Pro Glu Ser Leu Asn Cys
            115                 120                 125
Ser Lys Phe Pro Pro Gln Asn Asp His Asn His Met Cys Met Glu Gly
            130                 135                 140
Pro Gly Asp Glu Glu Val Pro Leu Pro His Lys Thr Pro Ile Gln Pro
145                 150                 155                 160
Gly Glu Glu Cys His Ser Val Gly Thr Asn Ser Asp Gln Tyr Ile Trp
                165                 170                 175
Val Lys Arg Ser Leu Asn Cys Val Leu Lys Cys Gly Tyr Asp Ala Gly
            180                 185                 190
Leu Tyr Ser Arg Ser Ala Lys Glu Phe Thr Asp Ile Trp Met Ala Val
            195                 200                 205
Trp Ala Ser Leu Cys Phe Ile Ser Thr Ala Phe Thr Val Leu Thr Phe
            210                 215                 220
Leu Ile Asp Ser Ser Arg Phe Ser Tyr Pro Glu Arg Pro Ile Ile Phe
225                 230                 235                 240
Leu Ser Met Cys Tyr Asn Ile Tyr Ser Ile Ala Tyr Ile Val Arg Leu
                245                 250                 255
Thr Val Gly Arg Glu Arg Ile Ser Cys Asp Phe Glu Glu Ala Ala Glu
            260                 265                 270
Pro Val Leu Ile Gln Glu Gly Leu Lys Asn Thr Gly Cys Ala Ile Ile
            275                 280                 285
Phe Leu Leu Met Tyr Phe Phe Gly Met Ala Ser Ser Ile Trp Trp Val
            290                 295                 300
Ile Leu Thr Leu Thr Trp Phe Leu Ala Ala Gly Leu Lys Trp Gly His
305                 310                 315                 320
Glu Ala Ile Glu Met His Ser Ser Tyr Phe His Ile Ala Ala Trp Ala
                325                 330                 335
Ile Pro Ala Val Lys Thr Ile Val Ile Leu Ile Met Arg Leu Val Asp
            340                 345                 350
Ala Asp Glu Leu Thr Gly Leu Cys Tyr Val Gly Asn Gln Asn Leu Asp
            355                 360                 365
Ala Leu Thr Gly Phe Val Val Ala Pro Leu Phe Thr Tyr Leu Val Ile
            370                 375                 380
Gly Thr Leu Phe Ile Ala Ala Gly Leu Val Ala Leu Phe Lys Ile Arg
385                 390                 395                 400
Ser Asn Leu Gln Lys Asp Gly Thr Lys Thr Asp Lys Leu Glu Arg Leu
                405                 410                 415
Met Val Lys Ile Gly Val Phe Ser Val Leu Tyr Thr Val Pro Ala Thr
            420                 425                 430
Cys Val Ile Ala Cys Tyr Phe Tyr Glu Ile Ser Asn Trp Ala Leu Phe
            435                 440                 445
```

-continued

```
Arg Tyr Ser Ala Asp Asp Ser Asn Met Ala Val Glu Met Leu Lys Ile
        450                 455                 460

Phe Met Ser Leu Leu Val Gly Ile Thr Ser Gly Met Trp Ile Trp Ser
465                 470                 475                 480

Ala Lys Thr Leu His Thr Trp Gln Lys Cys Ser Asn Arg Leu Val Asn
                485                 490                 495

Ser Gly Lys Val Lys Arg Glu Lys Arg Gly Asn Gly Trp Val Lys Pro
            500                 505                 510

Gly Lys Gly Ser Glu Thr Val Val Met Trp Pro Phe Ala Ser Val Pro
        515                 520                 525

Ala Gly Ala Lys Cys Arg Leu Val Glu Thr Leu Pro Glu Asn Met Asp
    530                 535                 540

Phe Arg Ser Asp His Leu Thr Thr Phe Glu Cys Phe Asn Glu Ile Ile
545                 550                 555                 560

Thr Leu Ala Lys Lys Tyr Ile Tyr Ile Ala Ser Phe Cys Cys Asn Pro
                565                 570                 575

Leu Ser Thr Thr Arg Gly Ala Leu Ile Phe Asp Lys Leu Lys Glu Ala
            580                 585                 590

Ser Glu Lys Gly Ile Lys Ile Val Leu Leu Asp Glu Arg Gly Lys
        595                 600                 605

Arg Asn Leu Gly Glu Leu Gln Ser His Cys Pro Asp Ile Asn Phe Ile
    610                 615                 620

Thr Val Asn Ile Asp Lys Lys Asn Val Gly Leu Leu Leu Gly Cys
625                 630                 635                 640

Phe Trp Val Ser Asp Asp Glu Arg Cys Tyr Val Gly Asn Ala Ser Phe
                645                 650                 655

Thr Gly Gly Ser Ile His Thr Ile Lys Thr Leu Gly Val Tyr Ser Asp
            660                 665                 670

Tyr Pro Pro Leu Ala Thr Asp Leu Arg Arg Arg Phe Asp Thr Phe Lys
        675                 680                 685

Ala Phe Asn Ser Ala Lys Asn Ser Trp Leu Asn Leu Cys Ser Ala Ala
    690                 695                 700

Cys Cys Leu Pro Val Ser Thr Ala Tyr His Ile Lys Asn Pro Ile Gly
705                 710                 715                 720

Gly Val Phe Phe Thr Asp Ser Pro Glu His Leu Leu Gly Tyr Ser Arg
                725                 730                 735

Asp Leu Asp Thr Asp Val Val Ile Asp Lys Leu Lys Ser Ala Lys Thr
            740                 745                 750

Ser Ile Asp Ile Glu His Leu Ala Ile Val Pro Thr Thr Arg Val Asp
        755                 760                 765

Gly Asn Ser Tyr Tyr Trp Pro Asp Ile Tyr Asn Ser Ile Ile Glu Ala
    770                 775                 780

Ala Ile Asn Arg Gly Val Lys Ile Arg Leu Leu Val Gly Asn Trp Asp
785                 790                 795                 800

Lys Asn Asp Val Tyr Ser Met Ala Thr Ala Arg Ser Leu Asp Ala Leu
                805                 810                 815

Cys Val Gln Asn Asp Leu Ser Val Lys Val Phe Thr Ile Gln Asn Asn
            820                 825                 830

Thr Lys Leu Leu Ile Val Asp Asp Glu Tyr Val His Ile Thr Ser Ala
        835                 840                 845

Asn Phe Asp Gly Thr His Tyr Gln Asn His Gly Phe Val Ser Phe Asn
    850                 855                 860
```

```
Ser Ile Asp Lys Gln Leu Val Ser Glu Ala Lys Lys Ile Phe Glu Arg
865                 870                 875                 880

Asp Trp Val Ser Ser His Ser Lys Ser Leu Lys Ile
                885                 890

<210> SEQ ID NO 3
<211> LENGTH: 728
<212> TYPE: PRT
<213> ORGANISM: Artificial Sequence
<220> FEATURE:
<223> OTHER INFORMATION: CXCR4-F13L Fusion Protein

<400> SEQUENCE: 3

Met Ala Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Ile
            35                  40                  45

Tyr Ser Ile Ile Phe Leu Thr Gly Ile Val Gly Asn Gly Leu Val Ile
        50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
        195                 200                 205

Met Val Gly Leu Ile Leu Pro Gly Ile Val Ile Leu Ser Cys Tyr Cys
210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335
```

Lys Arg Gly Gly His Ser Ser Val Ser Thr Glu Ser Glu Ser Ser Ser
                340                 345                 350

Phe His Ser Ser Met Trp Pro Phe Ala Ser Val Pro Ala Gly Ala Lys
        355                 360                 365

Cys Arg Leu Val Glu Thr Leu Pro Glu Asn Met Asp Phe Arg Ser Asp
        370                 375                 380

His Leu Thr Thr Phe Glu Cys Phe Asn Glu Ile Ile Thr Leu Ala Lys
385                 390                 395                 400

Lys Tyr Ile Tyr Ile Ala Ser Phe Cys Cys Asn Pro Leu Ser Thr Thr
                405                 410                 415

Arg Gly Ala Leu Ile Phe Asp Lys Leu Lys Glu Ala Ser Glu Lys Gly
        420                 425                 430

Ile Lys Ile Ile Val Leu Leu Asp Glu Arg Gly Lys Arg Asn Leu Gly
        435                 440                 445

Glu Leu Gln Ser His Cys Pro Asp Ile Asn Phe Ile Thr Val Asn Ile
        450                 455                 460

Asp Lys Lys Asn Asn Val Gly Leu Leu Leu Gly Cys Phe Trp Val Ser
465                 470                 475                 480

Asp Asp Glu Arg Cys Tyr Val Gly Asn Ala Ser Phe Thr Gly Gly Ser
                485                 490                 495

Ile His Thr Ile Lys Thr Leu Gly Val Tyr Ser Asp Tyr Pro Pro Leu
        500                 505                 510

Ala Thr Asp Leu Arg Arg Arg Phe Asp Thr Phe Lys Ala Phe Asn Ser
        515                 520                 525

Ala Lys Asn Ser Trp Leu Asn Leu Cys Ser Ala Ala Cys Cys Leu Pro
530                 535                 540

Val Ser Thr Ala Tyr His Ile Lys Asn Pro Ile Gly Gly Val Phe Phe
545                 550                 555                 560

Thr Asp Ser Pro Glu His Leu Leu Gly Tyr Ser Arg Asp Leu Asp Thr
                565                 570                 575

Asp Val Val Ile Asp Lys Leu Lys Ser Ala Lys Thr Ser Ile Asp Ile
        580                 585                 590

Glu His Leu Ala Ile Val Pro Thr Thr Arg Val Asp Gly Asn Ser Tyr
        595                 600                 605

Tyr Trp Pro Asp Ile Tyr Asn Ser Ile Ile Glu Ala Ala Ile Asn Arg
        610                 615                 620

Gly Val Lys Ile Arg Leu Leu Val Gly Asn Trp Asp Lys Asn Asp Val
625                 630                 635                 640

Tyr Ser Met Ala Thr Ala Arg Ser Leu Asp Ala Leu Cys Val Gln Asn
                645                 650                 655

Asp Leu Ser Val Lys Val Phe Thr Ile Gln Asn Asn Thr Lys Leu Leu
        660                 665                 670

Ile Val Asp Asp Glu Tyr Val His Ile Thr Ser Ala Asn Phe Asp Gly
        675                 680                 685

Thr His Tyr Gln Asn His Gly Phe Val Ser Phe Asn Ser Ile Asp Lys
        690                 695                 700

Gln Leu Val Ser Glu Ala Lys Lys Ile Phe Glu Arg Asp Trp Val Ser
705                 710                 715                 720

Ser His Ser Lys Ser Leu Lys Ile
                725

<210> SEQ ID NO 4
<211> LENGTH: 669
<212> TYPE: PRT

-continued

```
<213> ORGANISM: Artificial Sequence
<220> FEATURE:
<223> OTHER INFORMATION: CD20-F13L Fusion Protein

<400> SEQUENCE: 4

Met Ala Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro Met Trp Pro Phe Ala Ser Val
    290                 295                 300

Pro Ala Gly Ala Lys Cys Arg Leu Val Glu Thr Leu Pro Glu Asn Met
305                 310                 315                 320

Asp Phe Arg Ser Asp His Leu Thr Thr Phe Glu Cys Phe Asn Glu Ile
                325                 330                 335

Ile Thr Leu Ala Lys Lys Tyr Ile Tyr Ile Ala Ser Phe Cys Cys Asn
            340                 345                 350

Pro Leu Ser Thr Thr Arg Gly Ala Leu Ile Phe Asp Lys Leu Lys Glu
        355                 360                 365

Ala Ser Glu Lys Gly Ile Lys Ile Ile Val Leu Leu Asp Glu Arg Gly
    370                 375                 380

Lys Arg Asn Leu Gly Glu Leu Gln Ser His Cys Pro Asp Ile Asn Phe
```

```
             385                 390                 395                 400
    Ile Thr Val Asn Ile Asp Lys Lys Asn Asn Val Gly Leu Leu Leu Gly
                    405                 410                 415

Cys Phe Trp Val Ser Asp Asp Glu Arg Cys Tyr Val Gly Asn Ala Ser
                    420                 425                 430

Phe Thr Gly Gly Ser Ile His Thr Ile Lys Thr Leu Gly Val Tyr Ser
                    435                 440                 445

Asp Tyr Pro Pro Leu Ala Thr Asp Leu Arg Arg Arg Phe Asp Thr Phe
                450                 455                 460

Lys Ala Phe Asn Ser Ala Lys Asn Ser Trp Leu Asn Leu Cys Ser Ala
    465                 470                 475                 480

Ala Cys Cys Leu Pro Val Ser Thr Ala Tyr His Ile Lys Asn Pro Ile
                    485                 490                 495

Gly Gly Val Phe Phe Thr Asp Ser Pro Glu His Leu Leu Gly Tyr Ser
                    500                 505                 510

Arg Asp Leu Asp Thr Asp Val Val Ile Asp Lys Leu Lys Ser Ala Lys
                    515                 520                 525

Thr Ser Ile Asp Ile Glu His Leu Ala Ile Val Pro Thr Thr Arg Val
                    530                 535                 540

Asp Gly Asn Ser Tyr Tyr Trp Pro Asp Ile Tyr Asn Ser Ile Ile Glu
    545                 550                 555                 560

Ala Ala Ile Asn Arg Gly Val Lys Ile Arg Leu Leu Val Gly Asn Trp
                    565                 570                 575

Asp Lys Asn Asp Val Tyr Ser Met Ala Thr Ala Arg Ser Leu Asp Ala
                    580                 585                 590

Leu Cys Val Gln Asn Asp Leu Ser Val Lys Val Phe Thr Ile Gln Asn
                    595                 600                 605

Asn Thr Lys Leu Leu Ile Val Asp Asp Glu Tyr Val His Ile Thr Ser
                    610                 615                 620

Ala Asn Phe Asp Gly Thr His Tyr Gln Asn His Gly Phe Val Ser Phe
    625                 630                 635                 640

Asn Ser Ile Asp Lys Gln Leu Val Ser Glu Ala Lys Lys Ile Phe Glu
                    645                 650                 655

Arg Asp Trp Val Ser Ser His Ser Lys Ser Leu Lys Ile
                    660                 665

<210> SEQ ID NO 5
<211> LENGTH: 314
<212> TYPE: PRT
<213> ORGANISM: Artificial Sequence
<220> FEATURE:
<223> OTHER INFORMATION: A56R

<400> SEQUENCE: 5

Met Thr Arg Leu Pro Ile Leu Leu Leu Ile Ser Leu Val Tyr Ala
1               5                   10                  15

Thr Pro Phe Pro Gln Thr Ser Lys Lys Ile Gly Asp Asp Ala Thr Leu
                    20                  25                  30

Ser Cys Asn Arg Asn Asn Thr Asn Asp Tyr Val Val Met Ser Ala Trp
                    35                  40                  45

Tyr Lys Glu Pro Asn Ser Ile Ile Leu Leu Ala Ala Lys Ser Asp Val
                    50                  55                  60

Leu Tyr Phe Asp Asn Tyr Thr Lys Asp Lys Ile Ser Tyr Asp Ser Pro
65                  70                  75                  80

Tyr Asp Asp Leu Val Thr Thr Ile Thr Ile Lys Ser Leu Thr Ala Arg
```

```
                85                  90                  95
Asp Ala Gly Thr Tyr Val Cys Ala Phe Phe Met Thr Ser Thr Thr Asn
            100                 105                 110
Asp Thr Asp Lys Val Asp Tyr Glu Glu Tyr Ser Thr Glu Leu Ile Val
            115                 120                 125
Asn Thr Asp Ser Glu Ser Thr Ile Asp Ile Ile Leu Ser Gly Ser Thr
130                 135                 140
His Ser Pro Glu Thr Ser Ser Lys Lys Pro Asp Tyr Ile Asp Asn Ser
145                 150                 155                 160
Asn Cys Ser Ser Val Phe Glu Ile Ala Thr Pro Glu Pro Ile Thr Asp
                165                 170                 175
Asn Val Glu Asp His Thr Asp Thr Val Thr Tyr Thr Ser Asp Ser Ile
            180                 185                 190
Asn Thr Val Ser Ala Ser Ser Gly Glu Ser Thr Thr Asp Glu Thr Pro
            195                 200                 205
Glu Pro Ile Thr Asp Lys Glu Asp His Thr Val Thr Asp Thr Val Ser
            210                 215                 220
Tyr Thr Thr Val Ser Thr Ser Ser Gly Ile Val Thr Thr Lys Ser Thr
225                 230                 235                 240
Thr Asp Asp Ala Asp Leu Tyr Asp Thr Tyr Asn Asp Asn Asp Thr Val
                245                 250                 255
Pro Pro Thr Thr Val Gly Gly Ser Thr Thr Ser Ile Ser Asn Tyr Lys
            260                 265                 270
Thr Lys Asp Phe Val Glu Ile Phe Gly Ile Thr Ala Leu Ile Ile Leu
            275                 280                 285
Ser Ala Val Ala Ile Phe Cys Ile Thr Tyr Tyr Ile Tyr Asn Lys Arg
            290                 295                 300
Ser Arg Lys Tyr Lys Thr Glu Asn Lys Val
305                 310

<210> SEQ ID NO 6
<211> LENGTH: 370
<212> TYPE: PRT
<213> ORGANISM: Artificial Sequence
<220> FEATURE:
<223> OTHER INFORMATION: FZD-ECD-A56R Fusion Protein

<400> SEQUENCE: 6

Met Gly Trp Ser Cys Ile Ile Leu Phe Leu Val Ala Thr Ala Thr Gly
1               5                   10                  15
Ala His Ser Phe Gly Asp Glu Glu Glu Arg Arg Cys Asp Pro Ile Arg
            20                  25                  30
Ile Ser Met Cys Gln Asn Leu Gly Tyr Asn Val Thr Lys Met Pro Asn
        35                  40                  45
Leu Val Gly His Glu Leu Gln Thr Asp Ala Glu Leu Gln Leu Thr Thr
    50                  55                  60
Phe Thr Pro Leu Ile Gln Tyr Gly Cys Ser Ser Gln Leu Gln Phe Phe
65                  70                  75                  80
Leu Cys Ser Val Tyr Val Pro Met Cys Thr Glu Lys Ile Asn Ile Pro
                85                  90                  95
Ile Gly Pro Cys Gly Gly Met Cys Leu Ser Val Lys Arg Arg Cys Glu
            100                 105                 110
Pro Val Leu Lys Glu Phe Gly Phe Ala Trp Pro Glu Ser Leu Asn Cys
            115                 120                 125
Ser Lys Phe Pro Pro Gln Asn Asp His Asn His Met Cys Met Glu Gly
```

```
                130             135             140
Pro Gly Asp Glu Glu Val Pro Leu Pro His Lys Thr Pro Ile Gln Pro
145                 150                 155                 160

Gly Glu Glu Thr Ser Thr Thr Asn Asp Thr Asp Lys Val Asp Tyr Glu
                165                 170                 175

Glu Tyr Ser Thr Glu Leu Ile Val Asn Thr Asp Ser Glu Thr Ile
                180                 185                 190

Asp Ile Ile Leu Ser Gly Ser Thr His Ser Pro Glu Thr Ser Ser Lys
                195                 200                 205

Lys Pro Asp Tyr Ile Asp Asn Ser Asn Cys Ser Ser Val Phe Glu Ile
            210                 215                 220

Ala Thr Pro Glu Pro Ile Thr Asp Asn Val Glu Asp His Thr Asp Thr
225                 230                 235                 240

Val Thr Tyr Thr Ser Asp Ser Ile Asn Thr Val Ser Ala Ser Ser Gly
                245                 250                 255

Glu Ser Thr Thr Asp Glu Thr Pro Glu Pro Ile Thr Asp Lys Glu Asp
            260                 265                 270

His Thr Val Thr Asp Thr Val Ser Tyr Thr Thr Val Ser Thr Ser Ser
            275                 280                 285

Gly Ile Val Thr Thr Lys Ser Thr Thr Asp Asp Ala Asp Leu Tyr Asp
290                 295                 300

Thr Tyr Asn Asp Asn Asp Thr Val Pro Pro Thr Thr Val Gly Gly Ser
305                 310                 315                 320

Thr Thr Ser Ile Ser Asn Tyr Lys Thr Lys Asp Phe Val Glu Ile Phe
                325                 330                 335

Gly Ile Thr Ala Leu Ile Ile Leu Ser Ala Val Ala Ile Phe Cys Ile
                340                 345                 350

Thr Tyr Tyr Ile Tyr Asn Lys Arg Ser Arg Lys Tyr Lys Thr Glu Asn
                355                 360                 365

Lys Val
    370

<210> SEQ ID NO 7
<211> LENGTH: 855
<212> TYPE: PRT
<213> ORGANISM: Artificial Sequence
<220> FEATURE:
<223> OTHER INFORMATION: Her2-A56R Fusion Protein

<400> SEQUENCE: 7

Met Gly Trp Ser Cys Ile Ile Leu Phe Leu Val Ala Thr Ala Thr Gly
1               5                   10                  15

Ala His Ser Ser Thr Gln Val Cys Thr Gly Thr Asp Met Lys Leu Arg
                20                  25                  30

Leu Pro Ala Ser Pro Glu Thr His Leu Asp Met Leu Arg His Leu Tyr
            35                  40                  45

Gln Gly Cys Gln Val Val Gln Gly Asn Leu Glu Leu Thr Tyr Leu Pro
        50                  55                  60

Thr Asn Ala Ser Leu Ser Phe Leu Gln Asp Ile Gln Glu Val Gln Gly
65                  70                  75                  80

Tyr Val Leu Ile Ala His Asn Gln Val Arg Gln Val Pro Leu Gln Arg
                85                  90                  95

Leu Arg Ile Val Arg Gly Thr Gln Leu Phe Glu Asp Asn Tyr Ala Leu
                100                 105                 110

Ala Val Leu Asp Asn Gly Asp Pro Leu Asn Asn Thr Thr Pro Val Thr
```

```
            115                 120                 125
Gly Ala Ser Pro Gly Leu Arg Glu Leu Gln Leu Arg Ser Leu Thr
        130                 135                 140

Glu Ile Leu Lys Gly Gly Val Leu Ile Gln Arg Asn Pro Gln Leu Cys
145                 150                 155                 160

Tyr Gln Asp Thr Ile Leu Trp Lys Asp Ile Phe His Lys Asn Asn Gln
                165                 170                 175

Leu Ala Leu Thr Leu Ile Asp Thr Asn Arg Ser Arg Ala Cys His Pro
            180                 185                 190

Cys Ser Pro Met Cys Lys Gly Ser Arg Cys Trp Gly Glu Ser Ser Glu
        195                 200                 205

Asp Cys Gln Ser Leu Thr Arg Thr Val Cys Ala Gly Gly Cys Ala Arg
    210                 215                 220

Cys Lys Gly Pro Leu Pro Thr Asp Cys Cys His Glu Gln Cys Ala Ala
225                 230                 235                 240

Gly Cys Thr Gly Pro Lys His Ser Asp Cys Leu Ala Cys Leu His Phe
                245                 250                 255

Asn His Ser Gly Ile Cys Glu Leu His Cys Pro Ala Leu Val Thr Tyr
            260                 265                 270

Asn Thr Asp Thr Phe Glu Ser Met Pro Asn Pro Glu Gly Arg Tyr Thr
        275                 280                 285

Phe Gly Ala Ser Cys Val Thr Ala Cys Pro Tyr Asn Tyr Leu Ser Thr
    290                 295                 300

Asp Val Gly Ser Cys Thr Leu Val Cys Pro Leu His Asn Gln Glu Val
305                 310                 315                 320

Thr Ala Glu Asp Gly Thr Gln Arg Cys Glu Lys Cys Ser Lys Pro Cys
                325                 330                 335

Ala Arg Val Cys Tyr Gly Leu Gly Met Glu His Leu Arg Glu Val Arg
            340                 345                 350

Ala Val Thr Ser Ala Asn Ile Gln Glu Phe Ala Gly Cys Lys Lys Ile
        355                 360                 365

Phe Gly Ser Leu Ala Phe Leu Pro Glu Ser Phe Asp Gly Asp Pro Ala
    370                 375                 380

Ser Asn Thr Ala Pro Leu Gln Pro Glu Gln Leu Gln Val Phe Glu Thr
385                 390                 395                 400

Leu Glu Glu Ile Thr Gly Tyr Leu Tyr Ile Ser Ala Trp Pro Asp Ser
                405                 410                 415

Leu Pro Asp Leu Ser Val Phe Gln Asn Leu Gln Val Ile Arg Gly Arg
            420                 425                 430

Ile Leu His Asn Gly Ala Tyr Ser Leu Thr Leu Gln Gly Leu Gly Ile
        435                 440                 445

Ser Trp Leu Gly Leu Arg Ser Leu Arg Glu Leu Gly Ser Gly Leu Ala
    450                 455                 460

Leu Ile His His Asn Thr His Leu Cys Phe Val His Thr Val Pro Trp
465                 470                 475                 480

Asp Gln Leu Phe Arg Asn Pro His Gln Ala Leu Leu His Thr Ala Asn
                485                 490                 495

Arg Pro Glu Asp Glu Cys Val Gly Glu Gly Leu Ala Cys His Gln Leu
            500                 505                 510

Cys Ala Arg Gly His Cys Trp Gly Pro Gly Pro Thr Gln Cys Val Asn
        515                 520                 525

Cys Ser Gln Phe Leu Arg Gly Gln Glu Cys Val Glu Glu Cys Arg Val
    530                 535                 540
```

```
Leu Gln Gly Leu Pro Arg Glu Tyr Val Asn Ala Arg His Cys Leu Pro
545                 550                 555                 560

Cys His Pro Glu Cys Gln Pro Gln Asn Gly Ser Val Thr Cys Phe Gly
                565                 570                 575

Pro Glu Ala Asp Gln Cys Val Ala Cys Ala His Tyr Lys Asp Pro Pro
            580                 585                 590

Phe Cys Val Ala Arg Cys Pro Ser Gly Val Lys Pro Asp Leu Ser Tyr
        595                 600                 605

Met Pro Ile Trp Lys Phe Pro Asp Glu Glu Gly Ala Cys Gln Pro Cys
    610                 615                 620

Pro Ile Asn Cys Thr His Ser Cys Val Asp Leu Asp Asp Lys Gly Cys
625                 630                 635                 640

Pro Ala Glu Gln Arg Ala Ser Pro Thr Ser Thr Thr Asn Asp Thr Asp
                645                 650                 655

Lys Val Asp Tyr Glu Glu Tyr Ser Thr Glu Leu Ile Val Asn Thr Asp
            660                 665                 670

Ser Glu Ser Thr Ile Asp Ile Ile Leu Ser Gly Ser Thr His Ser Pro
        675                 680                 685

Glu Thr Ser Ser Lys Lys Pro Asp Tyr Ile Asp Asn Ser Asn Cys Ser
    690                 695                 700

Ser Val Phe Glu Ile Ala Thr Pro Glu Pro Ile Thr Asp Asn Val Glu
705                 710                 715                 720

Asp His Thr Asp Thr Val Thr Tyr Thr Ser Asp Ser Ile Asn Thr Val
                725                 730                 735

Ser Ala Ser Ser Gly Glu Ser Thr Thr Asp Glu Thr Pro Glu Pro Ile
            740                 745                 750

Thr Asp Lys Glu Asp His Thr Val Thr Asp Thr Val Ser Tyr Thr Thr
        755                 760                 765

Val Ser Thr Ser Ser Gly Ile Val Thr Thr Lys Ser Thr Thr Asp Asp
    770                 775                 780

Ala Asp Leu Tyr Asp Thr Tyr Asn Asp Asn Asp Thr Val Pro Pro Thr
785                 790                 795                 800

Thr Val Gly Gly Ser Thr Thr Ser Ile Ser Asn Tyr Lys Thr Lys Asp
                805                 810                 815

Phe Val Glu Ile Phe Gly Ile Thr Ala Leu Ile Ile Leu Ser Ala Val
            820                 825                 830

Ala Ile Phe Cys Ile Thr Tyr Tyr Ile Tyr Asn Lys Arg Ser Arg Lys
        835                 840                 845

Tyr Lys Thr Glu Asn Lys Val
    850                 855

<210> SEQ ID NO 8
<211> LENGTH: 935
<212> TYPE: PRT
<213> ORGANISM: Artificial Sequence
<220> FEATURE:
<223> OTHER INFORMATION: CD100-A56R Fusion Protein

<400> SEQUENCE: 8

Met Gly Trp Ser Cys Ile Ile Leu Phe Leu Val Ala Thr Ala Thr Gly
1               5                   10                  15

Ala His Ser Phe Ala Pro Ile Pro Arg Ile Thr Trp Glu His Arg Glu
            20                  25                  30

Val His Leu Val Gln Phe His Glu Pro Asp Ile Tyr Asn Tyr Ser Ala
        35                  40                  45
```

```
Leu Leu Leu Ser Glu Asp Lys Asp Thr Leu Tyr Ile Gly Ala Arg Glu
     50                  55                  60

Ala Val Phe Ala Val Asn Ala Leu Asn Ile Ser Glu Lys Gln His Glu
 65                  70                  75                  80

Val Tyr Trp Lys Val Ser Glu Asp Lys Ala Lys Cys Ala Glu Lys
                 85                  90                  95

Gly Lys Ser Lys Gln Thr Glu Cys Leu Asn Tyr Ile Arg Val Leu Gln
             100                 105                 110

Pro Leu Ser Ala Thr Ser Leu Tyr Val Cys Gly Thr Asn Ala Phe Gln
             115                 120                 125

Pro Ala Cys Asp His Leu Asn Leu Thr Ser Phe Lys Phe Leu Gly Lys
     130                 135                 140

Asn Glu Asp Gly Lys Gly Arg Cys Pro Phe Asp Pro Ala His Ser Tyr
145                 150                 155                 160

Thr Ser Val Met Val Asp Gly Glu Leu Tyr Ser Gly Thr Ser Tyr Asn
                 165                 170                 175

Phe Leu Gly Ser Glu Pro Ile Ile Ser Arg Asn Ser Ser His Ser Pro
             180                 185                 190

Leu Arg Thr Glu Tyr Ala Ile Pro Trp Leu Asn Glu Pro Ser Phe Val
     195                 200                 205

Phe Ala Asp Val Ile Arg Lys Ser Pro Asp Ser Pro Asp Gly Glu Asp
 210                 215                 220

Asp Arg Val Tyr Phe Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                 245                 250                 255

Gln Gly Gly Leu Arg Thr Leu Gln Lys Lys Trp Thr Ser Phe Leu Lys
             260                 265                 270

Ala Arg Leu Ile Cys Ser Arg Pro Asp Ser Gly Leu Val Phe Asn Val
     275                 280                 285

Leu Arg Asp Val Phe Val Leu Arg Ser Pro Gly Leu Lys Val Pro Val
     290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                 325                 330                 335

Lys Tyr Met Gln Ser Thr Thr Val Glu Gln Ser His Thr Lys Trp Val
             340                 345                 350

Arg Tyr Asn Gly Pro Val Pro Lys Pro Arg Pro Gly Ala Cys Ile Asp
     355                 360                 365

Ser Glu Ala Arg Ala Ala Asn Tyr Thr Ser Ser Leu Asn Leu Pro Asp
     370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                 405                 410                 415

Thr Gln Ile Val Val Asp Arg Thr Gln Ala Leu Asp Gly Thr Val Tyr
             420                 425                 430

Asp Val Met Phe Val Ser Thr Asp Arg Gly Ala Leu His Lys Ala Ile
     435                 440                 445

Ser Leu Glu His Ala Val His Ile Ile Glu Glu Thr Gln Leu Phe Gln
     450                 455                 460
```

-continued

```
Asp Phe Glu Pro Val Gln Thr Leu Leu Ser Ser Lys Lys Gly Asn
465                 470                 475                 480

Arg Phe Val Tyr Ala Gly Ser Asn Ser Gly Val Val Gln Ala Pro Leu
                485                 490                 495

Ala Phe Cys Gly Lys His Gly Thr Cys Glu Asp Cys Val Leu Ala Arg
            500                 505                 510

Asp Pro Tyr Cys Ala Trp Ser Pro Pro Thr Ala Thr Cys Val Ala Leu
        515                 520                 525

His Gln Thr Glu Ser Pro Ser Arg Gly Leu Ile Gln Glu Met Ser Gly
    530                 535                 540

Asp Ala Ser Val Cys Pro Asp Lys Ser Lys Gly Ser Tyr Arg Gln His
545                 550                 555                 560

Phe Phe Lys His Gly Gly Thr Ala Glu Leu Lys Cys Ser Gln Lys Ser
                565                 570                 575

Asn Leu Ala Arg Val Phe Trp Lys Phe Gln Asn Gly Val Leu Lys Ala
                580                 585                 590

Glu Ser Pro Lys Tyr Gly Leu Met Gly Arg Lys Asn Leu Leu Ile Phe
                595                 600                 605

Asn Leu Ser Glu Gly Asp Ser Gly Val Tyr Gln Cys Leu Ser Glu Glu
            610                 615                 620

Arg Val Lys Asn Lys Thr Val Phe Gln Val Val Ala Lys His Val Leu
625                 630                 635                 640

Glu Val Lys Val Val Pro Lys Pro Val Val Ala Pro Thr Leu Ser Val
                    645                 650                 655

Val Gln Thr Glu Gly Ser Arg Ile Ala Thr Lys Val Leu Val Ala Ser
            660                 665                 670

Thr Gln Gly Ser Ser Pro Pro Thr Pro Ala Val Gln Ala Thr Ser Ser
                675                 680                 685

Gly Ala Ile Thr Leu Pro Pro Lys Pro Ala Pro Thr Gly Thr Ser Cys
        690                 695                 700

Glu Pro Lys Ile Val Ile Asn Thr Val Pro Gln Leu His Ser Glu Lys
705                 710                 715                 720

Thr Met Tyr Leu Lys Ser Ser Asp Thr Ser Thr Thr Asn Asp Thr Asp
                725                 730                 735

Lys Val Asp Tyr Glu Glu Tyr Ser Thr Glu Leu Ile Val Asn Thr Asp
                740                 745                 750

Ser Glu Ser Thr Ile Asp Ile Ile Leu Ser Gly Ser Thr His Ser Pro
        755                 760                 765

Glu Thr Ser Ser Lys Lys Pro Asp Tyr Ile Asp Asn Ser Asn Cys Ser
    770                 775                 780

Ser Val Phe Glu Ile Ala Thr Pro Glu Pro Ile Thr Asp Asn Val Glu
785                 790                 795                 800

Asp His Thr Asp Thr Val Thr Tyr Thr Ser Asp Ser Ile Asn Thr Val
                805                 810                 815

Ser Ala Ser Ser Gly Glu Ser Thr Thr Asp Glu Thr Pro Glu Pro Ile
                820                 825                 830

Thr Asp Lys Glu Asp His Thr Val Thr Asp Thr Val Ser Tyr Thr Thr
        835                 840                 845

Val Ser Thr Ser Ser Gly Ile Val Thr Thr Lys Ser Thr Thr Asp Asp
    850                 855                 860

Ala Asp Leu Tyr Asp Thr Tyr Asn Asp Asn Asp Thr Val Pro Pro Thr
865                 870                 875                 880

Thr Val Gly Gly Ser Thr Thr Ser Ile Ser Asn Tyr Lys Thr Lys Asp
```

```
                    885                 890                 895
Phe Val Glu Ile Phe Gly Ile Thr Ala Leu Ile Ile Leu Ser Ala Val
                900                 905                 910

Ala Ile Phe Cys Ile Thr Tyr Tyr Ile Tyr Asn Lys Arg Ser Arg Lys
            915                 920                 925

Tyr Lys Thr Glu Asn Lys Val
    930                 935

<210> SEQ ID NO 9
<211> LENGTH: 317
<212> TYPE: PRT
<213> ORGANISM: Artificial Sequence
<220> FEATURE:
<223> OTHER INFORMATION: WR B5R Protein

<400> SEQUENCE: 9

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Val Leu Pro Ile Cys Val Arg Thr
225                 230                 235                 240

Asn Glu Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
```

<210> SEQ ID NO 10
<211> LENGTH: 243
<212> TYPE: PRT
<213> ORGANISM: Artificial Sequence
<220> FEATURE:
<223> OTHER INFORMATION: FZD-B5R (short)

<400> SEQUENCE: 10

```
Met Gly Trp Ser Cys Ile Ile Leu Phe Leu Val Ala Thr Ala Thr Gly
1               5                   10                  15

Ala Tyr Ala Phe Gly Asp Glu Glu Arg Arg Cys Asp Pro Ile Arg
            20                  25                  30

Ile Ser Met Cys Gln Asn Leu Gly Tyr Asn Val Thr Lys Met Pro Asn
        35                  40                  45

Leu Val Gly His Glu Leu Gln Thr Asp Ala Glu Leu Gln Leu Thr Thr
    50                  55                  60

Phe Thr Pro Leu Ile Gln Tyr Gly Cys Ser Ser Gln Leu Gln Phe Phe
65                  70                  75                  80

Leu Cys Ser Val Tyr Val Pro Met Cys Thr Glu Lys Ile Asn Ile Pro
                85                  90                  95

Ile Gly Pro Cys Gly Gly Met Cys Leu Ser Val Lys Arg Arg Cys Glu
            100                 105                 110

Pro Val Leu Lys Glu Phe Gly Phe Ala Trp Pro Glu Ser Leu Asn Cys
        115                 120                 125

Ser Lys Phe Pro Pro Gln Asn Asp His Asn His Met Cys Met Glu Gly
    130                 135                 140

Pro Gly Asp Glu Glu Val Pro Leu Pro His Lys Thr Pro Ile Gln Pro
145                 150                 155                 160

Gly Glu Glu Cys His Ser Val Gly Thr Asn Ser Asp Gln Tyr Ile Trp
                165                 170                 175

Val Lys Arg Ser Leu Asn Cys Val Leu Lys Cys Gly Tyr Asp Ala Gly
            180                 185                 190

Leu Tyr Ser Arg Ser Ala Lys Glu Cys Ala Thr Tyr His Ile Ile Ile
        195                 200                 205

Val Ala Leu Thr Ile Met Gly Val Ile Phe Leu Ile Ser Val Ile Val
    210                 215                 220

Leu Val Cys Ser Cys Asp Lys Asn Asn Asp Gln Tyr Lys Phe His Lys
225                 230                 235                 240

Leu Leu Pro
```

<210> SEQ ID NO 11
<211> LENGTH: 281
<212> TYPE: PRT
<213> ORGANISM: Artificial Sequence
<220> FEATURE:
<223> OTHER INFORMATION: FZD-B5R (long)

<400> SEQUENCE: 11

```
Met Gly Trp Ser Cys Ile Ile Leu Phe Leu Val Ala Thr Ala Thr Gly
1               5                   10                  15

Ala Tyr Ala Phe Gly Asp Glu Glu Arg Arg Cys Asp Pro Ile Arg
            20                  25                  30

Ile Ser Met Cys Gln Asn Leu Gly Tyr Asn Val Thr Lys Met Pro Asn
        35                  40                  45

Leu Val Gly His Glu Leu Gln Thr Asp Ala Glu Leu Gln Leu Thr Thr
```

```
            50                  55                  60
Phe Thr Pro Leu Ile Gln Tyr Gly Cys Ser Ser Gln Leu Gln Phe Phe
 65                  70                  75                  80

Leu Cys Ser Val Tyr Val Pro Met Cys Thr Glu Lys Ile Asn Ile Pro
                     85                  90                  95

Ile Gly Pro Cys Gly Gly Met Cys Leu Ser Val Lys Arg Arg Cys Glu
                100                 105                 110

Pro Val Leu Lys Glu Phe Gly Phe Ala Trp Pro Glu Ser Leu Asn Cys
            115                 120                 125

Ser Lys Phe Pro Pro Gln Asn Asp His Asn His Met Cys Met Glu Gly
        130                 135                 140

Pro Gly Asp Glu Glu Val Pro Leu Pro His Lys Thr Pro Ile Gln Pro
145                 150                 155                 160

Gly Glu Glu Cys His Ser Val Gly Thr Asn Ser Asp Gln Tyr Ile Trp
                165                 170                 175

Val Lys Arg Ser Leu Asn Cys Val Leu Lys Cys Gly Tyr Asp Ala Gly
            180                 185                 190

Leu Tyr Ser Arg Ser Ala Lys Glu Tyr Val Arg Thr Asn Glu Glu Phe
        195                 200                 205

Asp Pro Val Asp Asp Gly Pro Asp Asp Glu Thr Asp Leu Ser Lys Leu
210                 215                 220

Ser Lys Asp Val Val Gln Tyr Glu Gln Glu Ile Glu Ser Leu Glu Ala
225                 230                 235                 240

Thr Tyr His Ile Ile Ile Val Ala Leu Thr Ile Met Gly Val Ile Phe
                245                 250                 255

Leu Ile Ser Val Ile Val Leu Val Cys Ser Cys Asp Lys Asn Asn Asp
            260                 265                 270

Gln Tyr Lys Phe His Lys Leu Leu Pro
        275                 280

<210> SEQ ID NO 12
<211> LENGTH: 34
<212> TYPE: DNA
<213> ORGANISM: Artificial Sequence
<220> FEATURE:
<223> OTHER INFORMATION: MS4A1S

<400> SEQUENCE: 12
tataccatgg caacacccag aaattcagta aatg                              34

<210> SEQ ID NO 13
<211> LENGTH: 47
<212> TYPE: DNA
<213> ORGANISM: Artificial Sequence
<220> FEATURE:
<223> OTHER INFORMATION: MS4A1AS

<400> SEQUENCE: 13
ggtaccgatg caaatggcca cataggagag ctgtcatttt ctattgg                47

<210> SEQ ID NO 14
<211> LENGTH: 47
<212> TYPE: DNA
<213> ORGANISM: Artificial Sequence
<220> FEATURE:
<223> OTHER INFORMATION: F13S

<400> SEQUENCE: 14
ccaatagaaa atgacagctc tcctatgtgg ccatttgcat cggtacc                47
```

<210> SEQ ID NO 15
<211> LENGTH: 52
<212> TYPE: DNA
<213> ORGANISM: Artificial Sequence
<220> FEATURE:
<223> OTHER INFORMATION: F13AS

<400> SEQUENCE: 15
tatacgtacg ttaatggtga tggtgatgat gaatttttaa cgatttactg tg 52

<210> SEQ ID NO 16
<211> LENGTH: 506
<212> TYPE: PRT
<213> ORGANISM: Artificial Sequence
<220> FEATURE:
<223> OTHER INFORMATION: CD20-A56R Fusion Protein

<400> SEQUENCE: 16

```
Met Gly Trp Ser Cys Ile Ile Leu Phe Leu Val Ala Thr Ala Thr Gly
1               5                   10                  15

Ala His Thr Glu Leu Ile Val Asn Thr Asp Ser Glu Ser Thr Ile Asp
            20                  25                  30

Ile Ile Leu Ser Gly Ser Thr His Ser Pro Glu Thr Ser Ser Lys Lys
        35                  40                  45

Pro Asp Tyr Ile Asp Asn Ser Asn Cys Ser Ser Val Phe Glu Ile Ala
    50                  55                  60

Thr Pro Glu Pro Ile Thr Asp Asn Val Glu Asp His Thr Asp Thr Val
65                  70                  75                  80

Thr Tyr Thr Ser Asp Ser Ile Asn Thr Val Ser Ala Ser Ser Gly Glu
                85                  90                  95

Ser Thr Thr Asp Glu Thr Pro Glu Pro Ile Thr Asp Lys Glu Asp His
            100                 105                 110

Thr Val Thr Asp Thr Val Ser Tyr Thr Thr Val Ser Thr Ser Ser Gly
        115                 120                 125

Ile Val Thr Thr Lys Ser Thr Thr Asp Asp Ala Asp Leu Tyr Asp Thr
    130                 135                 140

Tyr Asn Asp Asn Asp Thr Val Pro Pro Thr Thr Val Gly Gly Ser Thr
145                 150                 155                 160

Thr Ser Ile Ser Asn Tyr Lys Thr Lys Asp Phe Val Glu Ile Phe Gly
                165                 170                 175

Ile Thr Ala Leu Ile Ile Leu Ser Ala Val Ala Ile Phe Cys Ile Thr
            180                 185                 190

Tyr Tyr Ile Tyr Asn Lys Arg Ser Arg Lys Tyr Lys Thr Glu Asn Lys
        195                 200                 205

Val Met Thr Thr Pro Arg Asn Ser Val Asn Gly Thr Phe Pro Ala Glu
    210                 215                 220

Pro Met Lys Gly Pro Ile Ala Met Gln Ser Gly Pro Lys Pro Leu Phe
225                 230                 235                 240

Arg Arg Met Ser Ser Leu Val Gly Pro Thr Gln Ser Phe Phe Met Arg
                245                 250                 255

Glu Ser Lys Thr Leu Gly Ala Val Gln Ile Met Asn Gly Leu Phe His
            260                 265                 270

Ile Ala Leu Gly Gly Leu Leu Met Ile Pro Ala Gly Ile Tyr Ala Pro
        275                 280                 285

Ile Cys Val Thr Val Trp Tyr Pro Leu Trp Gly Gly Ile Met Tyr Ile
    290                 295                 300
```

```
Ile Ser Gly Ser Leu Leu Ala Ala Thr Glu Lys Asn Ser Arg Lys Cys
305                 310                 315                 320

Leu Val Lys Gly Lys Met Ile Met Asn Ser Leu Ser Leu Phe Ala Ala
                325                 330                 335

Ile Ser Gly Met Ile Leu Ser Ile Met Asp Ile Leu Asn Ile Lys Ile
            340                 345                 350

Ser His Phe Leu Lys Met Glu Ser Leu Asn Phe Ile Arg Ala His Thr
        355                 360                 365

Pro Tyr Ile Asn Ile Tyr Asn Cys Glu Pro Ala Asn Pro Ser Glu Lys
    370                 375                 380

Asn Ser Pro Ser Thr Gln Tyr Cys Tyr Ser Ile Gln Ser Leu Phe Leu
385                 390                 395                 400

Gly Ile Leu Ser Val Met Leu Ile Phe Ala Phe Phe Gln Glu Leu Val
                405                 410                 415

Ile Ala Gly Ile Val Glu Asn Glu Trp Lys Arg Thr Cys Ser Arg Pro
            420                 425                 430

Lys Ser Asn Ile Val Leu Leu Ser Ala Glu Glu Lys Lys Glu Gln Thr
        435                 440                 445

Ile Glu Ile Lys Glu Glu Val Val Gly Leu Thr Glu Thr Ser Ser Gln
    450                 455                 460

Pro Lys Asn Glu Glu Asp Ile Glu Ile Ile Pro Ile Gln Glu Glu Glu
465                 470                 475                 480

Glu Glu Glu Thr Glu Thr Asn Phe Pro Glu Pro Pro Gln Asp Gln Glu
                485                 490                 495

Ser Ser Pro Ile Glu Asn Asp Ser Ser Pro
            500                 505

<210> SEQ ID NO 17
<211> LENGTH: 235
<212> TYPE: PRT
<213> ORGANISM: Artificial Sequence
<220> FEATURE:
<223> OTHER INFORMATION: HA-A56R Fusion Protein

<400> SEQUENCE: 17

Met Gly Trp Ser Cys Ile Ile Leu Phe Leu Val Ala Thr Ala Thr Gly
1               5                   10                  15

Ala His Ser Tyr Pro Tyr Asp Val Pro Asp Tyr Ala Thr Ser Thr Thr
            20                  25                  30

Asn Asp Thr Asp Lys Val Asp Tyr Glu Glu Tyr Ser Thr Glu Leu Ile
        35                  40                  45

Val Asn Thr Asp Ser Glu Ser Thr Ile Asp Ile Ile Leu Ser Gly Ser
    50                  55                  60

Thr His Ser Pro Glu Thr Ser Ser Lys Lys Pro Asp Tyr Ile Asp Asn
65                  70                  75                  80

Ser Asn Cys Ser Ser Val Phe Glu Ile Ala Thr Pro Glu Pro Ile Thr
                85                  90                  95

Asp Asn Val Glu Asp His Thr Asp Thr Val Thr Tyr Thr Ser Asp Ser
            100                 105                 110

Ile Asn Thr Val Ser Ala Ser Ser Gly Glu Ser Thr Thr Asp Glu Thr
        115                 120                 125

Pro Glu Pro Ile Thr Asp Lys Glu Asp His Thr Val Thr Asp Thr Val
    130                 135                 140

Ser Tyr Thr Thr Val Ser Thr Ser Ser Gly Ile Val Thr Thr Lys Ser
145                 150                 155                 160
```

```
Thr Thr Asp Asp Ala Asp Leu Tyr Asp Thr Tyr Asn Asp Asn Asp Thr
            165             170             175

Val Pro Pro Thr Thr Val Gly Gly Ser Thr Thr Ser Ile Ser Asn Tyr
            180             185             190

Lys Thr Lys Asp Phe Val Glu Ile Phe Gly Ile Thr Ala Leu Ile Ile
        195             200             205

Leu Ser Ala Val Ala Ile Phe Cys Ile Thr Tyr Tyr Ile Tyr Asn Lys
        210             215             220

Arg Ser Arg Lys Tyr Lys Thr Glu Asn Lys Val
225             230             235
```